(12) United States Patent
Wen et al.

(10) Patent No.: US 11,636,611 B2
(45) Date of Patent: Apr. 25, 2023

(54) SYSTEMS AND METHODS FOR IMAGE FUSION

(71) Applicant: SHANGHAI UNITED IMAGING HEALTHCARE CO., LTD., Shanghai (CN)

(72) Inventors: Linfei Wen, Shanghai (CN); Yanling Chen, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 25 days.

(21) Appl. No.: 16/686,560

(22) Filed: Nov. 18, 2019

(65) Prior Publication Data
US 2020/0211208 A1    Jul. 2, 2020

(30) Foreign Application Priority Data
Dec. 27, 2018   (CN) .......................... 201811612394.0

(51) Int. Cl.
*G06T 7/30*    (2017.01)
*G06T 5/50*    (2006.01)
*G06T 7/00*    (2017.01)

(52) U.S. Cl.
CPC .................. *G06T 7/30* (2017.01); *G06T 5/50* (2013.01); *G06T 7/0012* (2013.01);
(Continued)

(58) Field of Classification Search
CPC .......... G06T 7/30; G06T 5/50; G06T 7/0012; G06T 2207/10088; G06T 2207/20221; G06T 2207/30016; G06T 2207/10024; G06T 2207/30004; G06T 2207/10116; G06T 19/20; G06T 7/174
See application file for complete search history.

(56) References Cited

U.S. PATENT DOCUMENTS 8,774,485 B2    7/2014  Blaskovics et al.
2007/0237372 A1* 10/2007  Chen .................. G06V 10/7515
                                                                 382/128
(Continued)

FOREIGN PATENT DOCUMENTS

CN    102908142 A    2/2013
CN    103854270      6/2014
(Continued)

OTHER PUBLICATIONS

First Office Action in Chinese Application No. 201811612394.0 dated May 25, 2020, 13 pages.

*Primary Examiner* — Vu Le
*Assistant Examiner* — Winta Gebreslassie
(74) *Attorney, Agent, or Firm* — Metis IP LLC

(57) ABSTRACT

The present disclosure provides a system and method for image generation. The method may include obtaining a first image of a first modality representing a first region of a subject. The method may further include determining a second image of a second modality representing a second region of the subject based on the first image. The second region may include at least part of the first region of the subject. A slice direction of the first image may be the same as a slice direction of the second image. The method may further include generating a fused image by fusing the first image and the second image.

13 Claims, 14 Drawing Sheets

(52) U.S. Cl.
CPC ........... *G06T 2207/10088* (2013.01); *G06T 2207/20221* (2013.01); *G06T 2207/30016* (2013.01)

(56) References Cited

U.S. PATENT DOCUMENTS

| | | | |
|---|---|---|---|
| 2009/0292551 A1* | 11/2009 | Sirohey | G16H 30/40 705/2 |
| 2013/0129174 A1* | 5/2013 | Grbic | G06T 7/0012 382/131 |
| 2014/0119630 A1* | 5/2014 | Sowards-Emmerd | G06T 11/005 382/131 |
| 2016/0089055 A1 | 3/2016 | Rapoport | |
| 2017/0020489 A1 | 1/2017 | Kang et al. | |
| 2017/0164931 A1* | 6/2017 | Ng | A61B 8/5261 |
| 2019/0336033 A1* | 11/2019 | Takeshima | G01R 33/5608 |
| 2019/0350658 A1* | 11/2019 | Yang | A61B 6/032 |

FOREIGN PATENT DOCUMENTS

| | | |
|---|---|---|
| CN | 106580251 A | 4/2017 |
| CN | 107767444 | 3/2018 |

\* cited by examiner

SYSTEMS AND METHODS FOR IMAGE FUSION

CROSS-REFERENCE TO RELATED APPLICATIONS

This application claims priority of Chinese Patent Application No. 201811612394.0, filed on Dec. 27, 2018, the concentrations of which are hereby incorporated by reference.

TECHNICAL FIELD

The disclosure generally relates to imaging systems, and more particularly relates to systems and methods for image fusion.

BACKGROUND

Magnetic resonance spectroscopy (MRS) is a widely used non-invasive technique for the detection of metabolites of a human body. An MRS image may include functional information indicative of a distribution of one or more metabolites in a scanned object but does not include structural information indicative of one or more structural characteristics of the scanned object. In application of MRS, for example, to analyze lesions of a patient, an MRS image needs to be fused with a corresponding structural image (i.e., a scout image) (e.g., a magnetic resonance imaging (MRI) image, a computed tomography (CT) image, etc.) to improve an accuracy of diagnostic results. However, the fusion of the two images may fail if a scout image and an MRS image misalign. Therefore, it is desired to provide methods and systems for automatically generating a structural image that matches an MRS image to achieve image fusion.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a first image of a first modality representing a first region of a subject. The system may further determine, based on the first image, a second image of a second modality representing a second region of the subject. The second region may include at least part of the first region of the subject. A slice direction of the first image may be the same as a slice direction of the second image. The system may further generate a fused image by fusing the first image and the second image.

In some embodiments, to obtain a first image of a first modality representing a first region of a subject, the system may obtain one or more scout images of the first region of the subject. The system may cause an imaging device to acquire the first image by scanning the first region of the subject according to the one or more scout images.

In some embodiments, to determine, based on the first image, a second image of a second modality representing a second region of the subject, the system may determine whether one of the one or more scout images and the first image misalign. In response to a determination that the one of the one or more scout images and the first image misalign, the system may determine, based on the first image, the second image.

In some embodiments, to determine whether one of the one or more scout images and the first image misalign, the system may determine whether slice information of the one of the one or more scout images matches slice information of the first image. The slice information may include at least one of a slice position or a slice direction. The system may determine that the one of the one or more scout images and the first image misalign in response to a determination that the slice information of the one of the one or more scout images fails to match the slice information of the first image.

In some embodiments, to determine, based on the first image, a second image of a second modality representing a second region of the subject, the system may generate, based on the first image and the one of the one or more scout images, the second image.

In some embodiments, to determine, based on the first image, a second image of a second modality representing a second region of the subject, the system may obtain one or more third images of the second region. The one or more third images and the first image may be of different modalities. The system may further generate, based on the first image and the one or more third images, the second image.

In some embodiments, to determine, based on the first image, a second image of a second modality representing a second region of the subject, the system may cause an imaging device to acquire the second image by scanning the second region of the subject according to the first image.

In some embodiments, the first image may include a functional image indicative of a distribution of a metabolite in the first region, and the second image may include a structural image indicative of one or more structural characteristics of the second region.

In some embodiments, the first image may include a magnetic resonance spectroscopy (MRS) image.

In some embodiments, to generate a fused image by fusing the first image and the second image, the system may assign a value of each of at least some of a plurality of first pixels in the first image to a corresponding second pixel of a plurality of second pixels in the second image to obtain the fused image.

In some embodiments, to generate a fused image by fusing the first image and the second image, the system may convert the first image into a pseudocolor image. The system may further fuse the pseudocolor image and the second image to obtain the fused image.

In some embodiments, to fuse the pseudocolor image and the second image to obtain the fused image, the system may generate a registered pseudocolor image by registering the pseudocolor image with the second image. The system may further fuse the registered pseudocolor image and the second image to obtain the fused image.

In some embodiments, the first modality may be different from the second modality.

According to a second aspect of the present disclosure, a method is provided. The method may be implemented on at least one computing device, each of which may include at least one processor and a storage device. The method may include obtaining a first image of a first modality representing a first region of a subject, determining, based on the first image, a second image of a second modality representing a second region of the subject, the second region including at least part of the first region of the subject, a slice direction of the first image being same as a slice direction of the second image; and generating a fused image by fusing the first image and the second image.

According to a third aspect of the present disclosure, a non-transitory computer-readable medium storing at least one set of instructions is provided. When executed by at least one processor, the at least one set of instructions may direct the at least one processor to perform a method. The method may include obtaining a first image of a first modality representing a first region of a subject, determining, based on the first image, a second image of a second modality representing a second region of the subject, the second region including at least part of the first region of the subject, a slice direction of the first image being same as a slice direction of the second image; and generating a fused image by fusing the first image and the second image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
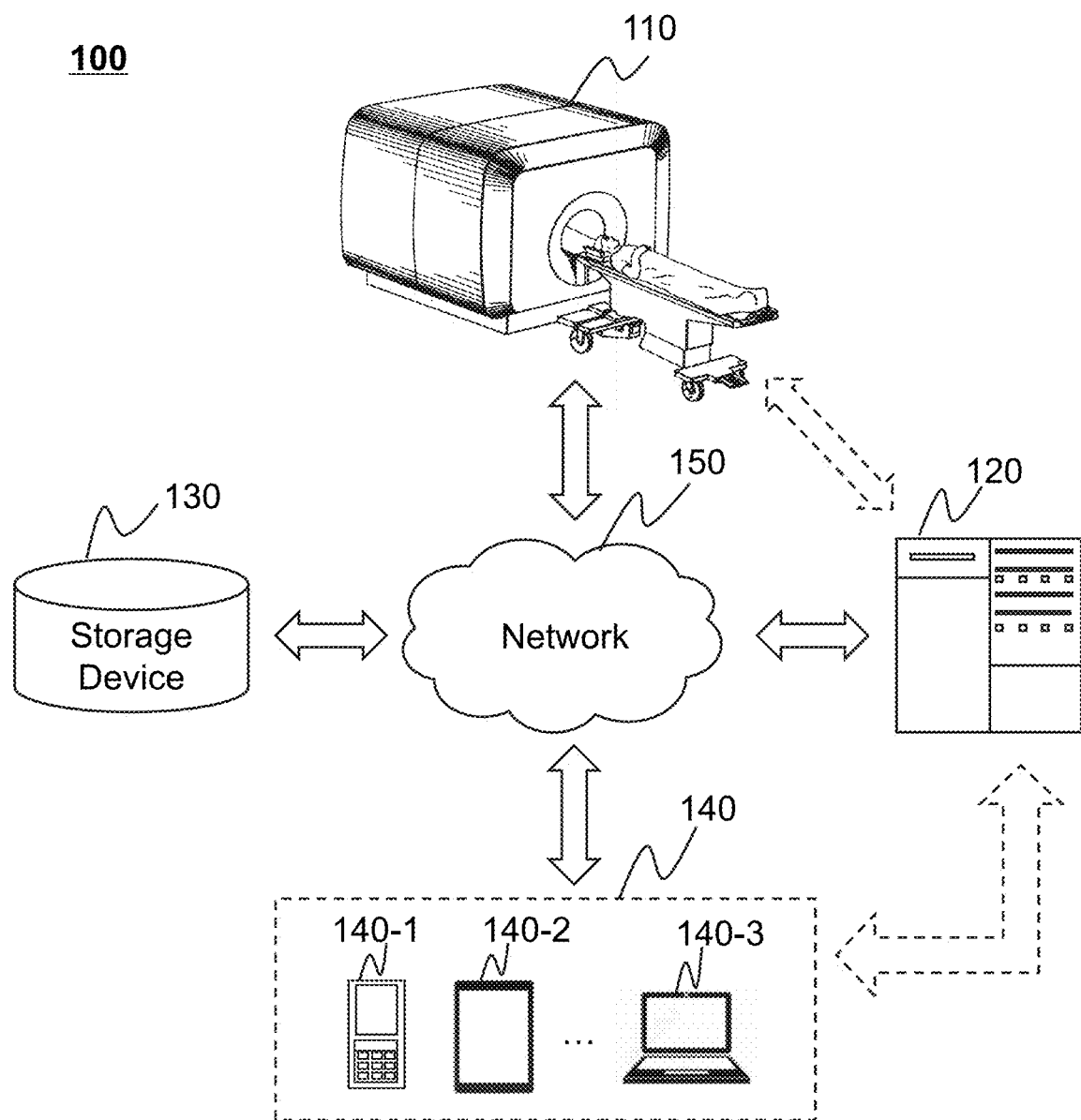
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Provided herein are systems and methods for image generation. A system may include at least one storage device storing executable instructions, and at least one processor in communication with the at least one storage device. When executing the executable instructions, the at least one processor may cause the system to obtain a first image of a first modality representing a first region of a subject. The first image may include a plurality of first pixels. The at least one processor may cause the system to determine a second image of a second modality representing a second region of the subject based on the first image. The second region may include at least part of the first region of the subject. A slice direction of the first image may be same as a slice direction of the second image. The second image may include a plurality of second pixels. The at least one processor may cause the system to generate a fused image by fusing the first image and the second image.

Accordingly, the system may automatically generate, based on the first image, the second image of a modality different from the first image. The first image and the second image may align, which may improve the accuracy of the fusion of the first image and the second image. In some embodiments, the first image of the first modality may be an MRS image of a subject, and the second image of the second modality may be an MR image of the subject. When the MRS image and the MR image misalign, the system may automatically obtain and/or reconstruct a reference image that matches the MRS image based on the MRS image and generate a target fused image based on the MRS image and the reference image. The target fused image may be more informative and/or accurate than the reference image and/or the MRS image. Accordingly, the target fused image of improved accuracy may facilitate doctors or other users to perform a diagnosis, assessment, and/or analysis on the basis of the target fused image.

FIG. 1 is a schematic diagram illustrating an exemplary imaging system according to some embodiments of the present disclosure. In some embodiments, the imaging system 100 may be a single-modality system or a multi-modality system. Exemplary single-modality systems may include a magnetic resonance imaging (MRI) system, a magnetic resonance spectroscopy (MRS) system, a positron emission tomography (PET) system, a computed tomography (CT) system, etc. Exemplary multi-modality systems may include a magnetic resonance-positron emission tomography (MR-PET) system, a positron emission tomography-computed tomography (PET-CT) system, etc. In some embodiments, the imaging system 100 may include modules and/or components for performing imaging and/or related analysis.

Merely by way of example, as illustrated in FIG. 1, the imaging system 100 may include a medical device 110, a processing device 120, a storage device 130, one or more terminals 140, and a network 150. The components in the imaging system 100 may be connected in one or more of various ways. Merely by way of example, the medical device 110 may be connected to the processing device 120 through the network 150. As another example, the medical device 110 may be connected to the processing device 120 directly as illustrated in FIG. 1. As a further example, the terminal(s) 140 may be connected to another component of the imaging system 100 (e.g., the processing device 120) via the network 150. As still a further example, the terminal(s) 140 may be connected to the processing device 120 directly as illustrated by the dotted arrow in FIG. 1. As still a further example, the storage device 130 may be connected to another component of the imaging system 100 (e.g., the processing device 120) directly as illustrated in FIG. 1, or through the network 150.

The medical device 110 may be configured to acquire imaging data relating to at least one part of a subject. The imaging data relating to at least one part of a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof.

In some embodiments, the medical device 110 may include a single modality imaging device. For example, the medical device 110 may include a magnetic resonance spectroscopy (MRS) device, a magnetic resonance imaging (MRI) device (also referred to as an MR device, an MR scanner), a positron emission tomography (PET) device, an emission computed tomography (ECT) device, a computed tomography (CT) device, a ultrasound device, or the like, or any combination thereof. In some embodiments, the medical device 110 may include a multi-modality imaging device. Exemplary multi-modality imaging devices may include an MRI-CT device, PET-CT device, a PET-MR device, or the like, or a combination thereof.

The processing device 120 may process data and/or information obtained from the medical device 110, the terminal(s) 140, and/or the storage device 130. For example, the processing device 120 may obtain a first image of a first modality representing a first region of a subject. The first image may include a plurality of first pixels. The processing device 120 may determine a second image of a second modality representing a second region of the subject based on the first image. The second region may include at least part of the first region of the subject. A slice direction of the first image may be the same as a slice direction of the second image. For example, the second region may enclose the first region. In other words, each first pixel in the first image representing the first region may correspond to a second pixel in the second image. A first pixel corresponding to a second pixel may refer to two pixels representing the same physical position or portion of the first region of the subject. The second image may include a plurality of second pixels. The processing device 120 may generate a fused image by fusing the first image and the second image. As another example, the processing device 120 may determine whether a scout image of the first region of the subject and the first image misalign. The processing device 120 may determine the second image based on the first image in response to a determination that the scout image and the first image misalign. As still another example, the processing device 120 may convert the first image into a pseudocolor image. The processing device 120 may generate a registered pseudocolor image by registering the pseudocolor image with the second image (or the reference image). The processing device 120 may fuse the registered pseudocolor image and the second image (or the reference image) to obtain the fused image.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical device 110, the terminal(s) 140, and/or the storage device 130 via the network 150. As another example, the processing device 120 may be directly connected to the medical device 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be part of the terminal(s) 140.

The storage device 130 may store data, instructions, and/or any other information. In some embodiments, the storage device 130 may store data obtained from the terminal(s) 140 and/or the processing device 120. The data may include image data acquired by the processing device 120, algorithms and/or models for processing the image data, etc. For example, the storage device 130 may store image data (e.g., MRS images, MR images, etc.) acquired by the medical device 110. As another example, the storage device 130 may store one or more algorithms for processing the image data, a trained machine learning model for image generation, etc. In some embodiments, the storage device 130 may store data and/or instructions that the processing device 120 may execute or use to perform exemplary methods/systems described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

In some embodiments, a user and/or an operator may operate the imaging system 100 using the terminal(s) 140. The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the medical device 110 (e.g., an MR device etc.), the terminal(s) 140, the processing device 120, the storage device 130, etc., may communicate information and/or data with one or more other components of the imaging system 100 via the network 150. For example, the processing device 120 may obtain data from the medical device 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios.

Figure 2:
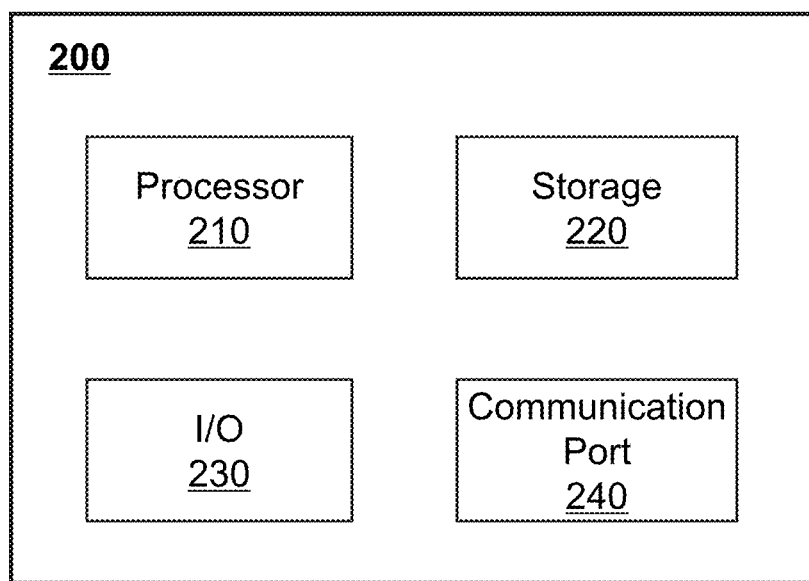
FIG. 2 is a schematic diagram illustrating hardware and/or software components of an exemplary computing device according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the medical device 110, the terminal(s) 140, the storage device 130, and/or any other component of the imaging system 100. Specifically, the processor 210 may process one or more measured data sets obtained from the medical device 110. For example, the processor 210 may generate an image based on the data set(s). In some embodiments, the generated image may be stored in the storage device 130, the storage 220, etc. In some embodiments, the generated image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for generating a fused image.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
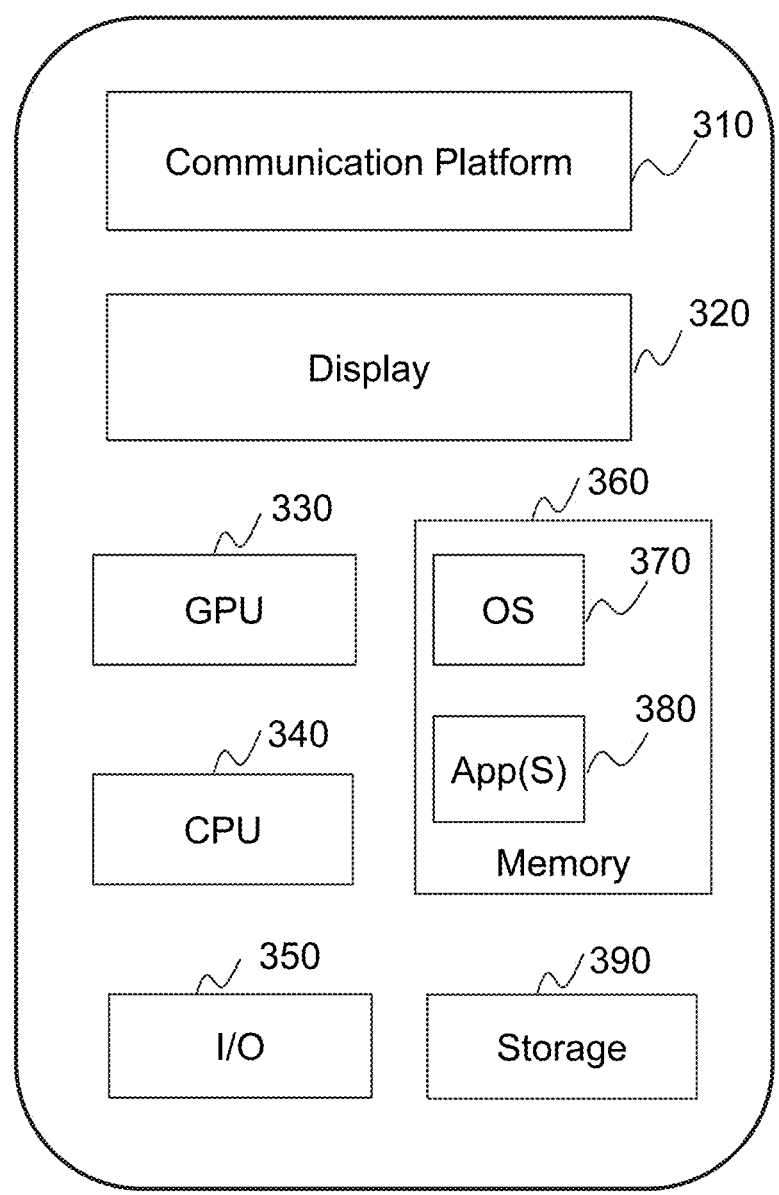
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
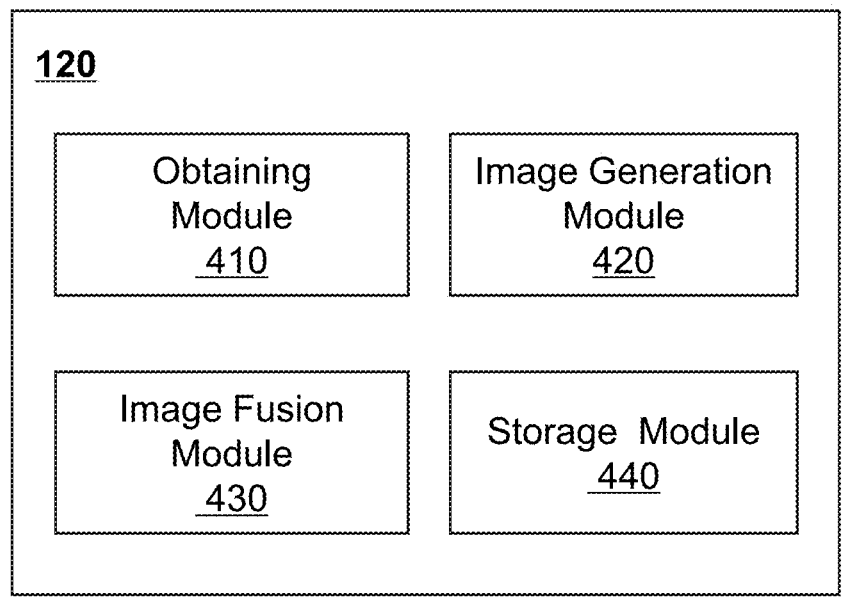
FIG. 4 is a block diagram illustrating an exemplary processing device according to some embodiments of the present disclosure.

FIG. 4 is a block diagram illustrating an exemplary processing device according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4, the processing device 120 may include an obtaining module 410, an image generation module 420, an image fusion module 430, and a storage module 440. Each of the modules described above may be a hardware circuit that is designed to perform certain actions, e.g., according to a set of instructions stored in one or more storage media, and/or any combination of the hardware circuit and the one or more storage media.

The obtaining module 410 may be configured to obtain data and/or information for image fusion. For example, the obtaining module 410 may obtain a first image and/or first raw imaging data (e.g., k-space data, projection data) of a first modality representing a first region of a subject. As another example, the obtaining module 410 may obtain a scout image of the first region of the subject. In some embodiments, the obtaining module 410 may obtain a model or algorithm for image fusion. For example, the obtaining module 410 may obtain an image reconstruction algorithm, an image registration algorithm, an image fusion algorithm, etc.

The image generation module 420 may be configured to determine a second image of a second modality representing a second region of the subject. The second image may include a representation of the second region of the subject. The second region may include at least part of the first region of the subject. A slice direction of the first image being same as a slice direction of the second image. In some embodiments, the image generation module 420 may determine the second image of the second modality based on the first slice information of the first image. For example, the processing device 120 may determine the second region (i.e., the scanning region) of the subject based on the first slice information of the first image. The processing device 120 may cause a second imaging device to scan the subject according to the scanning region using a second imaging technique to obtain the second image. In some embodiments, the image generation module 420 may determine the second image based on a scout image corresponding to the first image. For example, the image generation module 420 may process the scout image using an interpolation technique to obtain the second image. In some embodiments, the image generation module 420 may determine the second image based on one or more third images of the subject. The one or more third images may be obtained based on the first image. The first region of the subject may include at least part of a region (or a third region) of the subject represented in the one or more third images. The third modality may be different from the first modality The storage module 440 may be configured to store data and/or instructions associated with the imaging system 100. For example, the storage module 440 may store data of the first image acquired by a first imaging device, the second image acquired by a second imaging device, one or more algorithms used in image fusion (e.g., an image fusion algorithm, an image interpolation algorithm, an image registration algorithm, etc. In some embodiments, the storage module 440 may be the same as the storage device 130 and/or the storage module 480 in the configuration.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the image generation module 420 and the image fusion module 430 may be integrated into a single module. As another example, some other components/modules may be added into the processing device 120.

Figure 5:
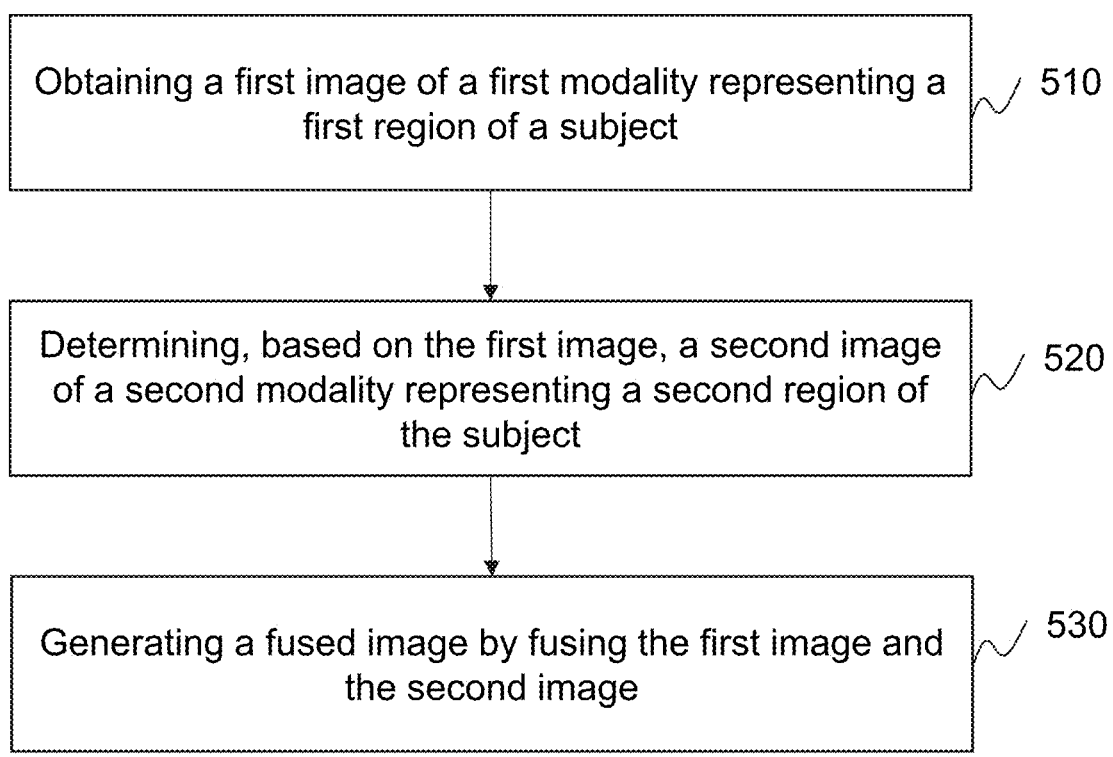
FIG. 5 is a schematic flowchart illustrating an exemplary process for generating a fused image according to some embodiments of the present disclosure.

FIG. 5 is a schematic flowchart illustrating an exemplary process for generating a fused image according to some embodiments of the present disclosure. In some embodiments, process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 510, the processing device 120 (e.g., the obtaining module 410) may obtain a first image of a first modality representing a first region of a subject. The subject may be biological or non-biological. For example, the subject may include a patient, a man-made object, etc. as described elsewhere in the present disclosure (e.g., FIG. 1 and the descriptions thereof). In some embodiments, the first image may be obtained from a first imaging device (e.g., the medical device 110), the storage device 130, or any other storage device. For example, the first image may be acquired by the first imaging device scanning the subject according to a scanning region (i.e., the first region) using a first scanning or imaging technique. As still another example, the processing device 120 may obtain first imaging data (e.g., projection data, k-space data) from the first imaging device (e.g., the medical device 110), the storage device 130, or any other storage device and generate the first image. The first imaging device may include an MR device, a PET device, a SPECT device, etc. For MR imaging, the scanning or imaging technique may include a conventional scanning technique and a functional scanning technique. Exemplary conventional scanning techniques may include a T1-weighted imaging technique, a T2-weighted imaging technique, an angiographic technique, a dynamic enhancement imaging technique, etc. Exemplary functional scanning techniques may include a diffusion-weighted imaging (DWI) technique, a perfusion-weighted imaging (PWI) technique, a magnetic resonance imaging (MRS) technique, an oxygen saturation level-dependent imaging (BOLD) technique, etc.

As used herein, a modality of a specific image (e.g., the first image) of a specific subject (e.g., the first region of the subject) may be defined by an imaging device acquiring the specific image, a scanning or imaging technique used by the imaging device scanning the specific subject, an image reconstruction technique for generating the specific image, or the like, or any combination thereof. Different images acquired by different scanning techniques may correspond to different modalities. For example, a functional image (e.g., an MRS image, a PET image, a SPET image, etc.) of a specific subject acquired using a functional scanning technique may be considered of a different modality than a structural image (e.g., an MR image, a CT image, etc.) of the specific subject acquired by a conventional scanning technique. As used herein, a functional image may provide functional information of a body, such as metabolism, blood flow, etc. A structural image may provide anatomic structural information, such as an edge or boundary, a shape, a size, etc. As another example, an MR image acquired using a T1 weighted imaging technique (i.e., T1 weighted image) may be considered of a different modality than another MR image acquired using a T2 weighted imaging technique (i.e., T2 weighted image). Different images of the same subject acquired by different imaging devices may correspond to different modalities. For example, an MR image of a specific subject obtained by an MR device may be considered of a different modality than a PET image of the specific subject obtained by a PET device. Different images of the same subject generated using different image reconstruction techniques based on the same imaging data (e.g., projection data) may correspond to different modalities. For example, an image generated using an image reconstruction technique (e.g., a back-projection technique) based on imaging data (e.g., projection data) may be considered of a different modality than another image generated using another image reconstruction technique (e.g., an iteration reconstruction technique) based on the same imaging data (e.g., projection data).

The first image may include a representation of the first region of the subject using a plurality of first pixels or voxels with pixel/voxel values or characteristics, e.g., luminance values, gray values, colors (or RGB values), saturation values, etc. Each of the plurality of first pixels or voxels corresponding to a physical position or portion of the first region of the subject. In some embodiments, the first image may include a functional image indicative of a distribution of one or more metabolites in the first region. For example, the first image may be an MRS image as illustrated in the FIG. 14. The first image may include first slice information. As used herein, slice information of an image associated with a specific subject may include information associated with a slice of the specific object represented in the image. The first image may be also referred to as a first image slice. Images described in the present disclosure may include slice information. For example, multiple images may be acquired when the specific subject is scanned using an MR device. Each image may correspond to a slice of the specific subject (e.g., the subject). The slice information of an image may include a slice position, a slice direction, a slice thickness, or the like, or any combination thereof. The slice position of an image may refer to a position of a slice represented in the image along an axis (e.g., a transverse axis, a sagittal axis, and/or a coronal axis) of an imaging device, that is, a position of an intersection point of the slice and the axis on the axis. The slice position may also be referred to as an axis position, e.g., a transverse position, a sagittal position, or a coronal position. The slice direction of an image may be defined by an angle between a slice represented in the image and an axial plane (e.g., a transverse plane, a sagittal plane, and/or a coronal plane) of the imaging device along a reference direction (e.g., clockwise or anti-clockwise). In some embodiments, the angle between the slice represented in the first image and the axial plane (e.g., the transverse plane, the sagittal plane, and/or the coronal plane) may be less than or equal to a first threshold. For example, the threshold may be equal to 1°, 0.5°, 0.1°, 0°, etc. In other words, the slice direction of the first image may be deemed to be parallel to the axial plane if the angle between the slice represented in the first image and the axial plane is less than or equal to the first threshold. In some embodiments, the angle between the slice represented in the first image and the axial plane (e.g., the transverse plane, the sagittal plane, and/or the coronal plane) may exceed a second threshold, such as 0°, 5°, 10°, 15°, 20°, etc. In other words, the slice direction of the first image and the axial plane may be deemed to misalign if the angle between the slice represented in the first image and the axial plane exceeds a second threshold. The slice thickness of an image may refer to a length of the scale represented in the image along a direction perpendicular to the slice direction of the image.

In 520, the processing device 120 (e.g., the image generation module 420) may determine a second image of a second modality representing a second region of the subject.

The second image may include a representation of the second region of the subject. The second image may include a plurality of second pixels or voxels corresponding to the second region. The second image may include second slice information. The second image may be also referred to as a second image slice. In some embodiments, if the slice thickness of the first image may be equal to the slice thickness of the second image, the second slice information may match the first slice information of the first image, i.e., the slice position and the slice direction of the second image may be same as the slice position and the slice direction of the first image. The second region may enclose at least part of the first region of the subject. For example, the second region may enclose the first region of the subject. Therefore each of the plurality of the first pixels or voxels may correspond to one of the plurality of the second pixels or voxels, such that the first image and the second image may align. As used herein, a first pixel corresponding to a second pixel may refer to that the two pixels correspond to the same physical position or portion of the subject. In some embodiments, if the slice thickness (e.g., 25 millimeters, 20 millimeters, etc.) of the first image exceeds the slice thickness (e.g., 5 millimeters) of the second image, the slice of the subject may include multiple sub-slices arranged along the slice direction of the first image. Each of the multiple sub-slices may include the same slice thickness as the slice of the second image. The direction of each of the multiple sub-slices may be the same as the slice direction of the first image. The second slice information may match slice information of one of the multiple sub-slices of the subject such that the second image and the one of the multiple sub-slices of the subject align. In other words, the slice position and the slice direction of the second image may be same as the position and the direction of the one of the multiple sub-slices of the subject. The second region may include at least a part of the first region of the subject. For example, the second region may be or include a part of the first region of the subject that corresponds to the one of the multiple sub-slices of the subject. Each of first pixels or voxels corresponding to the one of the multiple sub-slices of the subject may correspond to one of the plurality of the second pixels or voxels.

Figure 6:
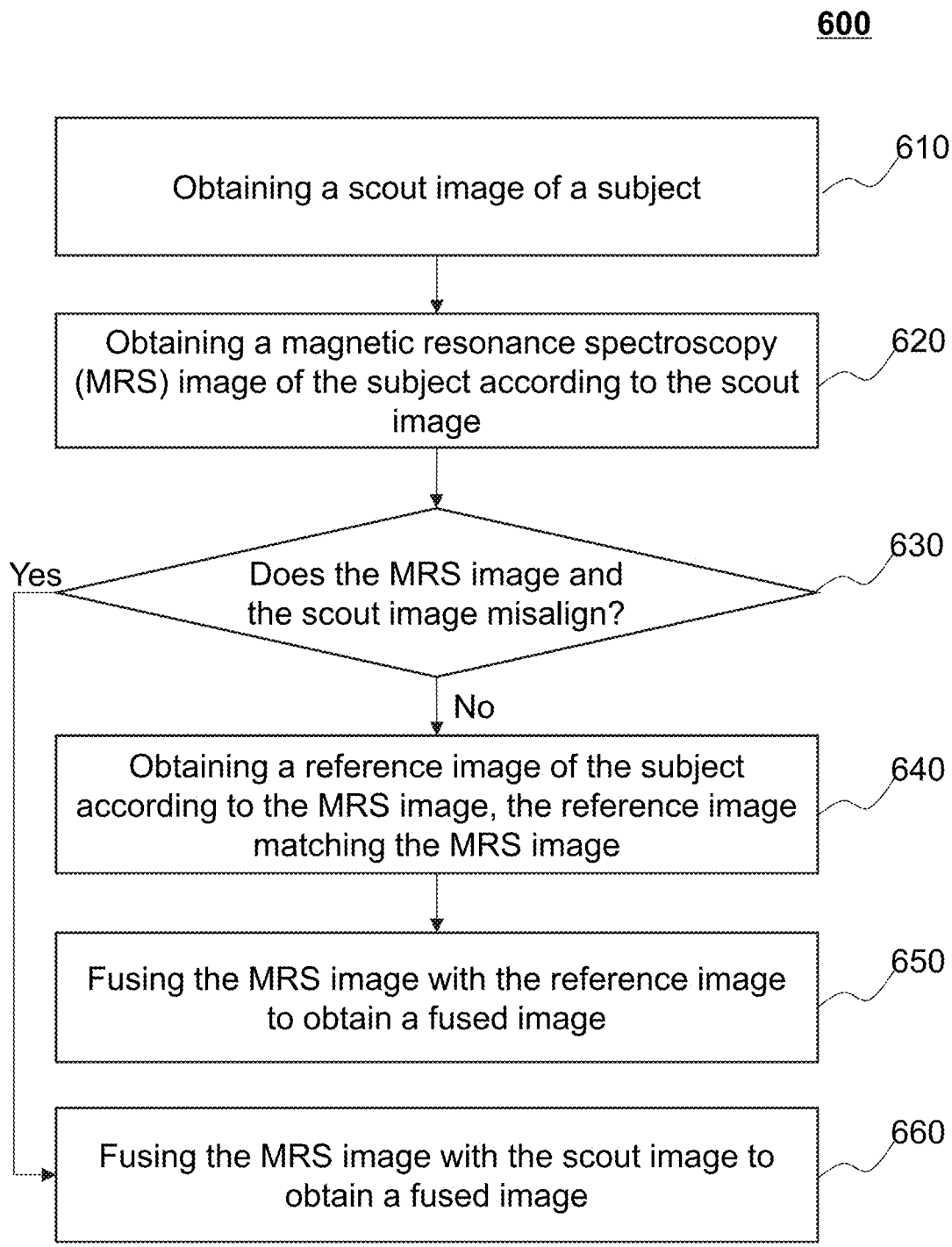
FIG. 6 is a schematic flowchart illustrating an exemplary process for generating a fused image according to some embodiments of the present disclosure.

In some embodiments, the second image may be also referred to as a reference image (e.g., the reference image as illustrated in FIG. 6) corresponding to the first image (e.g., the MRS image as illustrated in FIG. 6). In some embodiments, the second image may include a structural image indicative of one or more structural characteristics of the second region. Exemplary structural characteristics of the second region may include an edge or boundary, a size, a shape, etc., or a combination thereof, of the second region.

In some embodiments, the processing device 120 may determine the second image of the second modality based on the first slice information of the first image. For example, the processing device 120 may determine the second region (i.e., the scanning region) of the subject based on the first slice information of the first image. The processing device 120 may cause a second imaging device to scan the subject according to the scanning region using a second imaging technique to obtain the second image. The second modality may be different from the first modality. For example, the first imaging technique may include a functional imaging technique (e.g., an MRS imaging technique). The second imaging technique may include a conventional imaging technique (e.g., a T1 weighted imaging technique). As another example, the first imaging device may include a PET device. The second imaging device may include a CT device. As still another example, the first image reconstruction technique may include a T1 weighted imaging technique and the second image reconstruction technique may include a T2 weighted imaging technique.

In some embodiments, the processing device 120 may determine the second image based on one or more scout images corresponding to the first image. The one or more scout images corresponding to the first image may be used to determine a scanning region (i.e., the first region (e.g., region of interest) of the subject to obtain the first image. The scout image may be a CT image, an MR image, etc. In some embodiments, the processing device 120 may process the one or more scout images using an interpolation technique to obtain the second image. Further, the processing device 120 may perform an interpolation operation on the one or more scout images based on a deviation between the first slice information of the first image and slice information of the scout image. Exemplary interpolation techniques may include a scene-based interpolation technique, an object-based interpolation technique, or the like, or a combination thereof. Exemplary scene-based interpolation techniques may include a linear interpolation technique, a nearest neighbor interpolation technique, a spline interpolation technique, a Kriging interpolation technique, a polynomial interpolation technique, or the like, or any combination thereof. Exemplary object-based interpolation techniques may include a registration-based interpolation technique, a binary voxel-based interpolation technique, a nonrigid registration-based interpolation technique, or the like, or any combination thereof. In some embodiments, the processing device 120 may obtain scanning data (e.g., projection data, k-space data, etc.) that is used to reconstruct the one or more scout images. For example, the processing device 120 may obtain the scanning data corresponding to the one or more scout images from the storage device 130. As another example, the processing device 120 may transform the one or more scout images into the scanning data (e.g., projection data, k-space data, etc.) using an image transform technique, such as Fourier transform. The processing device 120 may reconstruct the second image based on the scanning data using an image reconstruction technique as described elsewhere in the present disclosure. More descriptions for determining the second image based on the one or more scout images may be found in FIG. 6.

In some embodiments, the processing device 120 may determine the second image based on one or more third images of the subject. The one or more third images may be obtained based on the first image. The first region of the subject may include at least part of a region (or a third region) of the subject represented in the one or more third images. The third modality may be different from the first modality. For example, the one or more third images may be acquired based on a conventional scanning technique, such as a T1 weighted imaging technique, a T2 weighted imaging technique, an angiographic technique, a dynamic enhancement imaging technique, etc. The first image may be acquired based on a functional scanning technique, such as a diffusion-weighted imaging (DWI) technique, a perfusion-weighted imaging (PWI) technique, a magnetic resonance imaging (MRS) technique, an oxygen saturation level-dependent imaging (BOLD) technique, etc. In some embodiments, third slice information of one of the third images may match or fail to match the first slice information of the first image. For example, the slice position of one of the third images may be different from the slice position of the first image. As another example, an angle between the first slice direction and the slice direction of one of the third images may be non-zero, such as 5°, 10°, 15°, 20°, etc.

In some embodiments, the processing device 120 may determine whether one of the third images and the first image misalign. If the processing device 120 determines that the one of the third images and the first image misalign, the processing device 120 may determine the second image by processing the third images using, for example, an interpolation technique. If the processing device 120 determines that one of the third images and the first image align, the processing device 120 may designate one of the third images as the second image. In some embodiments, the processing device 120 may determine that one of the third images and the first image align in response to a determination that the third slice information of the one of the third images matches the first slice information of the first image. The processing device 120 may determine that one of the third images and the first image misalign in response to a determination that the first slice information of the first image fails to match the third slice information of the one of the third images. As used herein, the misalignment of two images associated with a specific subject may refer to that at least one of a plurality of pixels (or voxels) in one of the two images does not correspond to one of a plurality of pixels (or voxels) in another one of the two images. The alignment of two images associated with a specific subject may refer to that a plurality of pixels (or voxels) in one of the two images correspond to a portion or whole of a plurality of pixels (or voxels) in another one of the two images. In some embodiments, the processing device 120 may obtain scanning data (e.g., projection data, k-space data, etc.) that is used to reconstruct the third images. For example, the processing device 120 may obtain the scanning data corresponding to the third images from the storage device 130. As another example, the processing device 120 may transform the third images into the scanning data (e.g., projection data, k-space data, etc.) using an image transform technique, such as Fourier transform. The processing device 120 may reconstruct the second image based on the scanning data corresponding to the one or more third images using an image reconstruction technique as described elsewhere in the present disclosure. More descriptions for generating the second image may be found in FIG. 6 and the descriptions thereof.

In 530, the processing device 120 (e.g., the obtaining module 410) may generate a fused image by fusing the first image and the second image. In some embodiments, the processing device 120 may generate the fused image using an image fusion technique. As used herein, the fusion of multiple images may be performed to integrate information from the multiple images (e.g., images of different modalities) into a single image (i.e., the fused image). Exemplary image fusion techniques may include a high pass filtering (HPF) technique, a wavelet transform technique, a principal component analysis (PCA) technique, a pair-wise spatial frequency matching technique, an IHS (intensity, hue, saturation) transform-based image fusion technique, a Laplacian pyramid technique, or the like, or any combination thereof. The fused image may include the functional information (e.g., the distribution of a metabolite) in the first image and the structural information (e.g., a shape, a size, an edge or boundary, etc.).

In some embodiments, before fusing the first image and the second image, the processing device 120 may register the first image and the second image using an image registration technique. The registration of multiple images may be performed to transform coordinate systems of the multiple images into a same coordinate system so that the corresponding points (e.g., pixels or voxels) in the multiple images reach spatial consistency, i.e., a same portion or position of a subject corresponds to the same portion of or spatial position on the multiple images. Exemplary image registration techniques may include a grayscale-based technique, a transform-domain based technique, a feature-based technique, or the like, or any combination thereof. Exemplary grayscale-based techniques may include using a sequential similarity detection algorithm (SSDA), a normalization cross-correlation (NCC) algorithm, a mean absolute differences (MAD) algorithm, a sum of squared differences (SSD) algorithm, etc. Exemplary transform-domain based technique may include using a Fourier transform (FT) based algorithm, a Walsh transform-based algorithm, a wavelet transform based algorithm, etc. Exemplary feature-based techniques may include using a point feature-based algorithm (e.g., a Harris operator), a line feature-based algorithm (e.g., a log operator), a region feature-based algorithm, etc. In some embodiments, using the image registration technique, the processing device 120 may determine a registration matrix describing a geometrical relationship between a coordinate system of the first image and a coordinate system of the second image based on multiple groups of feature points (e.g., contour points) in the first image and in the second image. Each of the multiple groups of feature points (e.g., contour points) in the first image and in the second image include a first pixel in the first image and a corresponding second pixel in the second image. The processing device 120 may transform the first image (or the second image) into a registered first image (or a registered second image) based on the registration matrix.

In some embodiments, the processing device 120 may assign a value of each of at least a portion of the plurality of first pixels or voxels in the first image (or the registered first image) to a corresponding second pixel or voxel in the second image (or the registered second image) to obtain the fused image. For example, the processing device 120 may determine a metabolite of a specific type (or referred to as a specific metabolite) from metabolites of other types of the subject. The processing device 120 may assign a value of a concentration of the specific metabolite corresponding to each of at least a portion of the plurality of first pixels or voxels to a corresponding second pixel or voxel in the second image. As another example, the processing device 120 may determine a metabolite of a first type (or referred to as a first metabolite) and a metabolite of a second type (or referred to as a second metabolite) from the one or more metabolites of the subject. The processing device 120 may determine a relationship between the first metabolite and the second metabolite (e.g., a ratio of a concentration of the first metabolite to a concentration of the second metabolite) of each of the plurality of the first pixels or voxels. The processing device 120 may assign a value associated with the relationship (e.g., the ratio) corresponding to each of at least a portion of the plurality of first pixels or voxels in the first image to a corresponding second pixel or voxel in the second image. The processing device 120 may cause a terminal to display the fused image.

In some embodiments, the processing device 120 may assign a color of each of at least some of the plurality of the first pixels or voxels to a corresponding second pixel or voxel of the plurality of second pixels or voxels to obtain the fused image. For example, the processing device 120 may convert the first image (or the first registered image) into a pseudocolor image based on the distribution of one of the one or more metabolites. The processing device 120 may generate the fused image by fusing the pseudocolor image and the second image. More descriptions for generating the fused image may be found in FIG. 7 and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 510 and operation 520 may be combined into a single operation. As another example, one or more other optional operations (e.g., a storing operation) may be added elsewhere in the process 500. In the storing operation, the processing device 120 may store information and/or data (e.g., the first image, the second image, the fused image, etc.) associated with the imaging system 100 in a storage device (e.g., the storage device 130) disclosed elsewhere in the present disclosure.

FIG. 6 is a schematic flowchart illustrating an exemplary process for generating a fused image according to some embodiments of the present disclosure. In some embodiments, process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 120 (e.g., the obtaining module 410) may obtain a scout image of a subject. The subject may be associated with a person or an animal, or a portion thereof. For example, the subject may include a patient. As another example, the subject may include a specific portion, organ, and/or tissue of the patient. Exemplary organs may include the head, the neck, the thorax, the heart, the stomach, the liver, a lung, a kidney, etc. Exemplary tissues may include epithelial tissue, a connective tissue, a nervous tissue, a muscular tissue, etc. In some embodiments, the scout image may be obtained from an imaging device (e.g., the medical device 110), the storage device 130, or any other storage device. For example, the imaging device may transmit acquired raw imaging data (e.g., projection data, k-space data) to the storage device 130, the storage module 440, or any other storage device for storage. The processing device 120 may obtain the raw imaging data from the storage device 130, the storage module 440, or any other storage device and generate the scout image based on the raw imaging data. As another example, the processing device 120 may obtain the scout image or the raw imaging data from the imaging device directly.

In some embodiments, the scout image may be generated using an image reconstruction technique based on the raw imaging data (e.g., projection data). The raw imaging data and the scout image may include information associated with structural (or anatomical structure) features of the subject. In some embodiments, the raw imaging data may include MR imaging data, CT imaging data, PECT imaging data, DR imaging data, ultrasound imaging data, or the like, or any combination thereof. For example, for MR imaging data, the scout image generated based on the MR imaging data (e.g., k-space data) may include a fast scout MR image, a T1 weighted image, a T2 weighted image, a diffusion-weighted MR image, a perfusion-weighted MR image, a mapping MR image, etc. In some embodiments, the raw imaging data may be two-dimensional (2D) imaging data, a three-dimensional (3D) imaging data, a four-dimensional (4D) imaging data, or the like, or any combination thereof. In some embodiments, the image reconstruction technique may include using a Fourier transform (FT) reconstruction, an iterative reconstruction, a backward projection (e.g., a convolution back-projection (CBP) technique, a filtering back-projection (FBP) technique), or the like, or any combination thereof.

The scout image may be used to determine and/or define a scanning region for a next scan (e.g., an MRS scan). The scout image may include slice information (also referred to as scout slice information). The scout slice information may include a scout slice position, a scout slice direction, etc. In some embodiments, an angle between the scout slice represented in the scout image and an axial plane (e.g., the transverse plane, the sagittal plane, and/or the coronal plane) of the imaging device may be equal to 0°. In other words, the scout slice direction may be parallel to the axial plane. In some embodiments, the angle between the scout slice represented in the scout image and the axial plane (e.g., the transverse plane, the sagittal plane, and/or the coronal plane) of the imaging device may be non-zero, such as 5°, 10°, 15°, 20°, etc. In other words, the scout slice direction and the axial plane may misalign.

In some embodiments, the scout image may be an MR image. The scout image may be determined from one or more MR images generated by an MR device scanning the subject manually, semi-automatically, or automatically. For example, the processing device 120 may obtain the one or more MR images corresponding to one or more slices of the subject based on the raw MR imaging data. The one or more MR images may be displayed on a client terminal (e.g., the terminal(s) 140). A user (e.g., a doctor) may select an MR image from the one or more MR images as the scout image according to clinical experience. In some embodiments, the user may determine and/or mark a portion of the selected MR image as a region of interest (ROI). The selected MR image with the marked ROI may be designated as the scout image. The ROI may be used to define a scanning region of the subject for a next scan (e.g., an MRS scan). As another example, the processing device 120 may determine one of the one or more MR images as the scout image according to a default setting of the imaging system 100. In some embodiments, the user may select an MR image as the scout image affording one single axial view. In some embodiments, the user may select two or more MR images affording multiple axial views, e.g., a transverse view, a sagittal view, and/or a coronal view, respectively. The processing device 120 may determine the scout image (e.g., a 3D image) based on the two or more MR images. For example, the user may select a slice affording each of the transverse view, a sagittal view, and the coronal view. The processing device 120 may determine the scout image (3D scout image) based on the MR images corresponding to the selected slices to obtain a 3D scanning region.

In 620, the processing device 120 (e.g., the obtaining module 410) may obtain a magnetic resonance spectroscopy (MRS) image of the subject according to the scout image. In some embodiments, the MRS image may be obtained from an MR device, the processing device 120, the storage device 130, or any other storage device. For example, the MR device may transmit acquired MRS imaging data to the storage device 130, the storage module 440, or any other storage device for storage. The processing device 120 may obtain the MRS imaging data from the storage device 130, the storage module 440, or any other storage device and generate the MRS image based on the MRS imaging data. As another example, the processing device 120 may obtain the MRS image from the MR device directly. The MRS imaging data may be acquired by the MR device via scanning the subject according to the scanning region (i.e., the ROI region) that may be determined based on the slice information of the scout image.

Slice information of the MRS image (also referred to as MRS slice information) may match or fail to match the slice information of the scout image. For example, the slice position of the MRS image (i.e., MRS slice position) may be different from the scout slice position of the scout image, but the scout slice direction may be the same as the slice direction of the MRS image (i.e., MRS slice direction). As another example, an angle between the scout slice direction and the MRS slice direction may be non-zero, such as 5°, 10°, 15°, 20°, etc., but the MRS slice position may be same as the scout slice position. As still another example, the MRS slice position may be the same as the scout slice position and the scout slice direction may be the same as the MRS slice direction. In some embodiments, the MRS slice information may fail to match the slice information of the scout image due to, for example, one or more scanning parameters of the MR device being adjusted during the scanning subject. More descriptions for the misalign between the slice information of the scout image and the MRS image may be found elsewhere in the present disclosure (e.g., FIGS. 8-10 and the descriptions thereof). For example, to avoid scanning areas including, such as blood vessels, bones, cavities, and/or tissue interfaces, etc., one or more scanning parameters may be adjusted which may cause a deviation or misalign between the scanning region determined based on the scout image (i.e., a desired scanning region) and the scanning region corresponding to the MRS image (i.e., an actual scanning region).

The actual scanning region corresponding to the MRS image may be also referred to as a first region of the subject. The MRS image may include a plurality of first pixels or voxels corresponding to the first region of the subject. The MRS image may be indicative of a distribution of one or more metabolites in the first region of the subject. For example, a first pixel (or voxel) value of each of the plurality of first pixels (or voxels) may denote a concentration of a metabolite, such as, an N-acetyl aspartate (NAA), a creatine (Cr), a choline (Cho), a lactate (Lac), an adenosine triphosphate (ATP), etc., in different portions of the ROI of the subject. As another example, the MRS image may be denoted as a concentration matrix indicative of a distribution of concentration of one kind of metabolite, such as, N-acetyl aspartate (NAA), creatine (Cr), choline (Cho), lactate (Lac), adenosine triphosphate (ATP), etc., in different portions of the first region of the subject. As still another example, the MRS image may be denoted as a concentration matrix indicative of a distribution of a relationship of multiple metabolites in different portions of the first region of the subject.

In 630, the processing device 120 (e.g., the image generation module 420) may determine whether the MRS image and the scout image misalign. In response to a determination that the MRS image and the scout image align, the processing device 120 may proceed to perform operation 660. In response to a determination that the MRS image and the scout image misalign, the processing device 120 may proceed to perform operation 640. As used herein, the scout image aligning with the MRS image may refer to that each of the plurality of first pixels or voxels in the MRS image corresponds to one of a plurality of pixels or voxels in the scout image. The scout image and the MRS image misalign may refer to that at least one of the plurality of first pixels or voxels in the MRS image does not correspond to one of the plurality of pixels or voxels in the scout image. Two corresponding pixels in the scout image and the MRS image may correspond to or represent the same position or position of the subject.

In some embodiments, the processing device 120 may determine whether the scout image and the MRS image misalign based on the slice information of the scout image and the MRS image. For example, the processing device 120 may compare the MRS slice information and the scout slice information. The processing device 120 may deem that the MRS image and the scout image align in response to a determination that the MRS slice information matches the scout slice information. The processing device 120 may deem that the MRS image and the scout image misalign in response to a determination that the scout slice information fails to match the MRS slice information. The scout slice information failing to match the MRS slice information may also refer to that the scout slice information of the image is different from the MRS slice information. For example, the processing device 120 may deem that the MRS slice information fails to match the scout slice information in response to a determination that at least one of the MRS slice position or the MRS slice direction is different from the scout slice position or the scout slice direction. The processing device 120 may deem that the MRS slice information matches the scout slice information in response to a determination that the MRS slice position and the MRS slice direction are the same as the scout slice position or the scout slice direction. More descriptions regarding the misalignment or alignment between the scout image and the MRS image may be found elsewhere in the present disclosure (e.g. FIGS. 8 to 10 or FIGS. 11 to 13 and the descriptions thereof).

In 640, the processing device 120 (e.g., the image generation module 420) may obtain a reference image of the subject according to the MRS image. The reference image may include slice information (i.e., reference slice information) matching the MRS slice information, i.e., the slice position and the slice direction of the reference image may be the same as the slice position and the slice direction of the MRS image. The reference image may include a representation of a specific region (also referred to as a second region) of the subject. The second region may enclose the first region of the subject. In some embodiments, the reference image may include a plurality of second pixels or voxels corresponding to the second region. Each of the plurality of the first pixels or voxels may correspond to one of the plurality of the second pixels or voxels. In other words, the reference image and the MRS image may align. More descriptions regarding the match of the slice information between the reference image and the MRS image may be found elsewhere in the present disclosure (e.g. FIGS. 11 to 13 and the descriptions thereof).

In some embodiments, the processing device 120 may cause a specific imaging device (e.g., the medical device 110) to acquire the reference image by scanning a specific subject according to the MRS image. For example, in response to a determination that the scout image and the MRS image misalign, the imaging device may automatically scan the subject based on the MRS slice information. Specifically, the processing device 120 may determine a reference scanning region based on the slice information of the MRS image. The processing device 120 may cause the specific imaging device to scan the subject according to the reference scanning region to obtain reference imaging data. The processing device 120 may obtain the reference imaging data and generate the reference image. In some embodiments, the specific imaging device may be the same as or different from the imaging device that acquires the scout image or the imaging device that acquires the MRS image. For example, the imaging device that acquires the scout image may be an MR device, and the specific imaging device may also be an MR device. As another example, the imaging device that acquires the scout image may be an MR device and the specific imaging device may be a CT device. In some embodiments, the reference image and the scout image may be acquired using the same imaging technique. For example, both the reference image and the scout image may be images such as a fast scout MR image, a T1 weighted image, a T2 weighted image, a diffusion-weighted MR image, a perfusion-weighted MR image, a mapping MR image, etc. In some embodiments, the reference image and the scout image may be acquired using different imaging techniques. For example, the scout image may be a T1 weighted image, and the reference image may be a T2 weighted image. As another example, the scout image may be a T2 weighted image, and the reference image may be a perfusion-weighted MR image.

In some embodiments, the processing device 120 may generate the reference image by processing the scout image based on the MRS slice information. For example, in response to a determination that the scout image and the MRS image misalign, the processing device 120 may process the scout image using an interpolation technique. Using the interpolation technique, the processing device 120 may modify pixel values of the plurality of pixels in the scout image to obtain the reference image, i.e., pixel values of the plurality of second pixels. Specifically, the processing device 120 may determine an interpolation function based on a deviation between the MRS slice information and the scout slice information. The processing device 120 may use the interpolation function to process the pixel values of the plurality of pixels in the scout image to obtain the reference image. The interpolation function may describe a relationship between the pixel values of the plurality of second pixels and pixel values of the plurality of pixels in the scout image. The interpolation function may include one or more coefficients. The one or more coefficients may be associated with the deviation between the slice information of the MRS image and the slice information of the scout image. For example, the one or more coefficients may be associated with a distance between the scout slice position and the MRS slice position, an angle between the scout slice direction and the MRS slice direction, etc. In some embodiments, the interpolation technique may include a scene-based interpolation technique, an object-based interpolation technique, or the like, or a combination thereof. Exemplary scene-based interpolation techniques may include a linear interpolation technique, a nearest neighbor interpolation technique, a spline interpolation technique, a Kriging interpolation technique, a polynomial interpolation technique, or the like, or any combination thereof. Exemplary object-based interpolation techniques may include a registration-based interpolation technique, a binary voxel-based interpolation technique, a nonrigid registration-based interpolation technique, or the like, or any combination thereof. In some embodiments, the processing device 120 may reconstruct the reference image based on scan data (e.g., projection data, k-space data, etc.) corresponding to the scout image and the slice information of the MRS image.

In some embodiments, the processing device 120 may determine the reference image based on an additional image of the subject. The additional image may be of a modality different from the MRS image. For example, the additional image may be a fast scout MR image, a T1 weighted image, a T2 weighted image, a diffusion-weighted MR image, a perfusion-weighted MR image, a mapping MR image, etc. In some embodiments, slice information of the additional image may match the MRS slice information, the processing device 120 may designate the additional image as the reference image. In some embodiments, slice information of the additional image may fail to match the MRS slice information, the processing device 120 may process the additional image using an interpolation technique to obtain the reference image. In some embodiments, the processing device 120 may reconstruct the reference image based on scan data (e.g., projection data, k-space data, etc.) corresponding to the additional image and the slice information of the MRS image.

In 650, the processing device 120 (e.g., the image fusion module 430) may fuse the MRS image with the reference image to obtain a fused image. As described in the present disclosure, the MRS image may include concentration information of one of the one or more metabolites of the subject, and the reference image may include structural information of the subject. The pixel values plurality of second pixels in the reference image may be denoted by gray values. The gray value of a second pixel may indicate a relaxation time of a portion of the subject corresponding to the second pixel. Densities of different portions of the subject may be determined based on the relaxation time corresponding to each of the plurality of the second pixels. Since the reference slice information matches the MRS slice information, each of the plurality of the first pixels in the MRS image may correspond to one of the plurality of the second pixels in the reference image, such that the MRS image and the reference image may be fused to obtain the fused image. In some embodiments, the processing device 120 may transmit the fused image to a terminal (e.g., the terminal(s) 140 in the imaging system 100) for display.

In some embodiments, before fusing the MRS image and the reference image, the processing device 120 may register the MRS image and/or the reference image using an image registration technique as described elsewhere in the present disclosure (e.g., FIG. 5 and the descriptions thereof). For example, the processing device 120 may register the MRS image based on the reference image to obtain a registered MRS image. The processing device 120 may fuse the registered MRS image with the reference image. As another example, the processing device 120 may register the reference image based on the MRS image to obtain a registered reference image. The processing device 120 may fuse the registered reference image with the MRS image. In some embodiments, the processing device 120 may generate the fused image by using an image fusion technique as described elsewhere in the present disclosure (e.g., FIG. 5 and the descriptions thereof).

In some embodiments, the processing device 120 may assign a value of each of at least some of the plurality of first pixels or voxels to a corresponding second pixel or voxel of the plurality of second pixels or voxels to obtain the fused image as described elsewhere in the present disclosure (e.g., FIG. 5 and the descriptions thereof). For example, the processing device 120 may determine a specific metabolite from the one or more metabolites. The processing device 120 may assign a value or a color representing a concentration of the specific metabolite corresponding to each of at least a portion of the plurality of first pixels or voxels of the MRS image to a corresponding second pixel or voxel of the reference image. The processing device 120 may cause a terminal to display the fused image with the values or colors corresponding to the at least a portion of the plurality of first pixels or voxels. For example, the processing device 120 may convert the MRS image into a pseudocolor image based on the distribution of the one or more metabolites. The processing device 120 may generate a registered pseudocolor image by registering the pseudocolor image with the reference image. The processing device 120 may generate the fused image by fusing the registered pseudocolor image and the reference image. More descriptions for generating the fused image based on the pseudocolor image and the reference image may be found in FIG. 7 and the descriptions thereof.

In 660, the processing device 120 (e.g., the image fusion module 430) may fuse the MRS image with the scout image to obtain a fused image. In some embodiments, the processing device 120 may fuse the scout image and the MRS image using an image fusion technique as described elsewhere in the present disclosure (e.g., FIG. 5 and the descriptions thereof). For example, the processing device 120 may assign a value or a color of each of at least a portion of the plurality of first pixels or voxels to a corresponding second pixel or voxel of the plurality of second pixels or voxels to obtain the fused image. As another example, before fusing the MRS image and the scout image, the processing device 120 may register the MRS image and the scout image using an image registration technique as described elsewhere in the present disclosure.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 610 and operation 620 may be combined into a single operation. As another example, one or more other optional operations (e.g., a storing operation) may be added elsewhere in the process 600. In the storing operation, the processing device 120 may store information and/or data (e.g., the scout image, the MRS image, the reference image, the fused image, etc.) associated with the imaging system 100 in a storage device (e.g., the storage device 130) disclosed elsewhere in the present disclosure.

Figure 7:
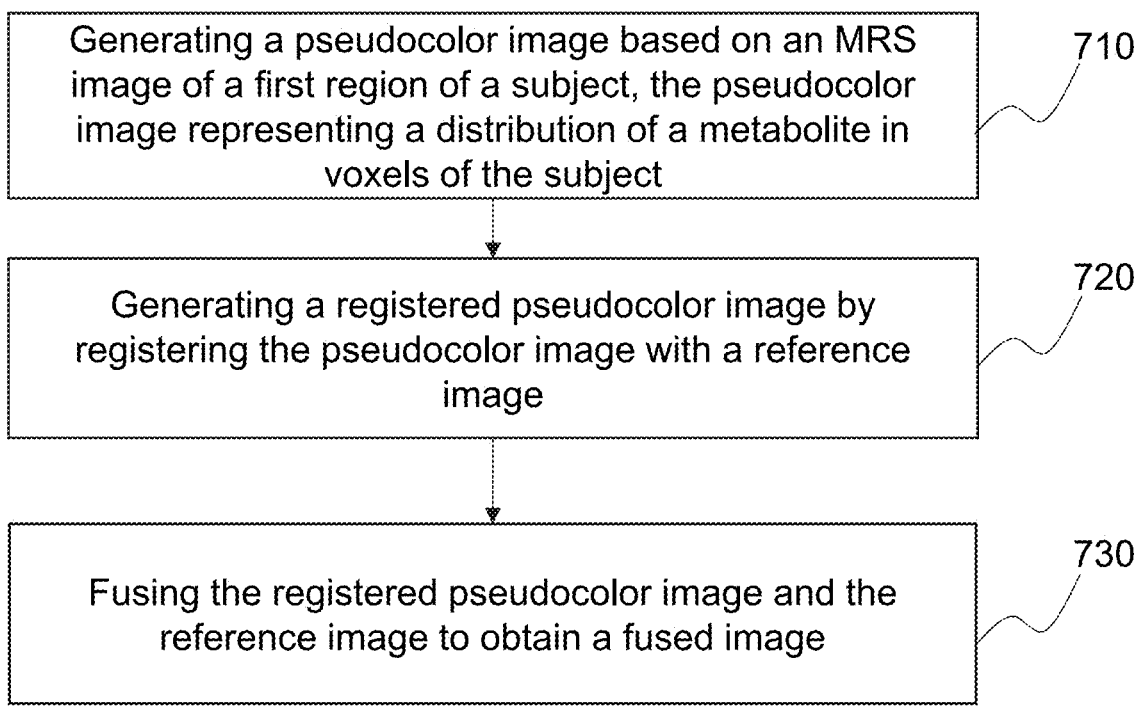
FIG. 7 is a schematic flowchart illustrating an exemplary process for generating a fused image according to some embodiments of the present disclosure.

FIG. 7 is a schematic flowchart illustrating an exemplary process for generating a fused image according to some embodiments of the present disclosure. In some embodiments, process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 710, the processing device 120 (e.g., the image fusion module 430) may generate a pseudocolor image based on an MRS image of a subject. The MRS image may include a plurality of first pixels or voxels representing a distribution of a specific metabolite (e.g., NAA) of the subject as described in connection with operation 620 in FIG. 6. The pseudocolor image may include a plurality of specific pixels or voxels each of which may correspond to a first pixel or voxel. The colors (or pixel values) of the plurality of specific pixels or voxels in the pseudocolor image may represent the distribution of the specific metabolite. A color (or pixel value) of a pixel in the pseudocolor image does not represent values of primary colors (e.g., red (R), green (G), blue (B)) of the portion or position of the subject that corresponds to the pixel or voxel but may serve as an index or code of the pixel or voxel, in which the index or code points to an entry of a color look-up table (CLUT). Therefore, the color of a pixel in the pseudocolor image may be also referred to as a pseudocolor. The actual color of each of the plurality of specific pixels or voxels may be obtained by querying the CLUT based on the index or code of the pseudocolor image. For example, a specific pixel value in the pseudocolor image may point to a specific entry in the CLUT. If the specific entry in the CLUT contains a Red/Green/Blue triplet (255, 0, 0), the actual color of the specific pixel value may be red. A pseudocolor of a pixel or voxel in the pseudocolor image, or its corresponding actual color determined based on the pseudocolor and the CLUT, may demonstrate the concentration value of a metabolite at a portion or position of the subject.

In some embodiments, the processing device 120 may convert the MRS image into the pseudocolor image using a pseudocolor image transformation algorithm (e.g., a gray level division algorithm, a gray level transformation algorithm, etc.). For example, the processing device 120 may determine a mapping relationship between a concentration value of a specific metabolite at a portion or position of the subject represented by a pixel or voxel in the MRS image and a pseudocolor (described in terms of, e.g., a combination of the primary colors) corresponding to a pixel or voxel in the pseudocolor image. The processing device 120 may convert the MRS image into the pseudocolor image based on the mapping relationship.

In 720, the processing device 120 (e.g., the image fusion module 430) may generate a registered pseudocolor image by registering the pseudocolor image with a reference image. In some embodiments, the processing device 120 may register the pseudocolor image with the reference image using an image registration technique. In some embodiments, the image registration technique may include a grayscale-based technique, a transform-domain based technique, a feature-based technique, or the like, or any combination thereof. In some embodiments, using the image registration technique, the processing device 120 may determine a registration matrix based on multiple groups of feature points (e.g., contour points) in the MRS image and the reference image. Each of the multiple groups of feature points (e.g., contour points, corner points) in the MRS image and the reference image include a first pixel in the first image and a corresponding second pixel in the second image. The feature points may be determined using a feature extraction algorithm (e.g., the Harris corner detection algorithm, a random sample consensus (RANSAC) algorithm, etc.). The processing device 120 may transform the pseudocolor image into the registered pseudocolor image based on the registration matrix.

In 730, the processing device 120 (e.g., the image fusion module 430) may fuse the registered pseudocolor image and the reference image to obtain a fused image. The fused image may include information associated with the one or more structural characteristics of the subject and information associated with the distribution of the one or more metabolites. In some embodiments, the processing device 120 may transmit the fused image to a terminal (e.g., the terminal(s) 140 in the imaging system 100) for display.

In some embodiments, the processing device 120 may generate the fused image by assigning a value or a color of each of the plurality of the specific pixels in the registered pseudocolor image to a corresponding second pixel of the plurality of second pixels to obtain the fused image. In some embodiments, the processing device 120 may generate the fused image by using an image fusion operation. In some embodiments, the image fusion operation may include using a high pass filtering (HPF) technique, a wavelet transform technique, a principal component analysis (PCA) technique, a pair-wise spatial frequency matching technique, an IHS (intensity, hue, saturation) transform-based image fusion technique, a Laplacian pyramid technique, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 720 and operation 730 may be combined into a single operation. As another example, one or more other optional operations (e.g., a storing operation) may be added elsewhere in the process 700. In the storing operation, the processing device 120 may store information and/or data (e.g., the pseudocolor image, the registered pseudocolor image, the fused image, etc.) associated with the imaging system 100 in a storage device (e.g., the storage device 130) disclosed elsewhere in the present disclosure.

EXAMPLES

The following examples are provided for illustration purposes and are not intended to limit the scope of the present disclosure. FIGS. 8-18 were obtained based on scans performed on the same subject.

Figure 8:
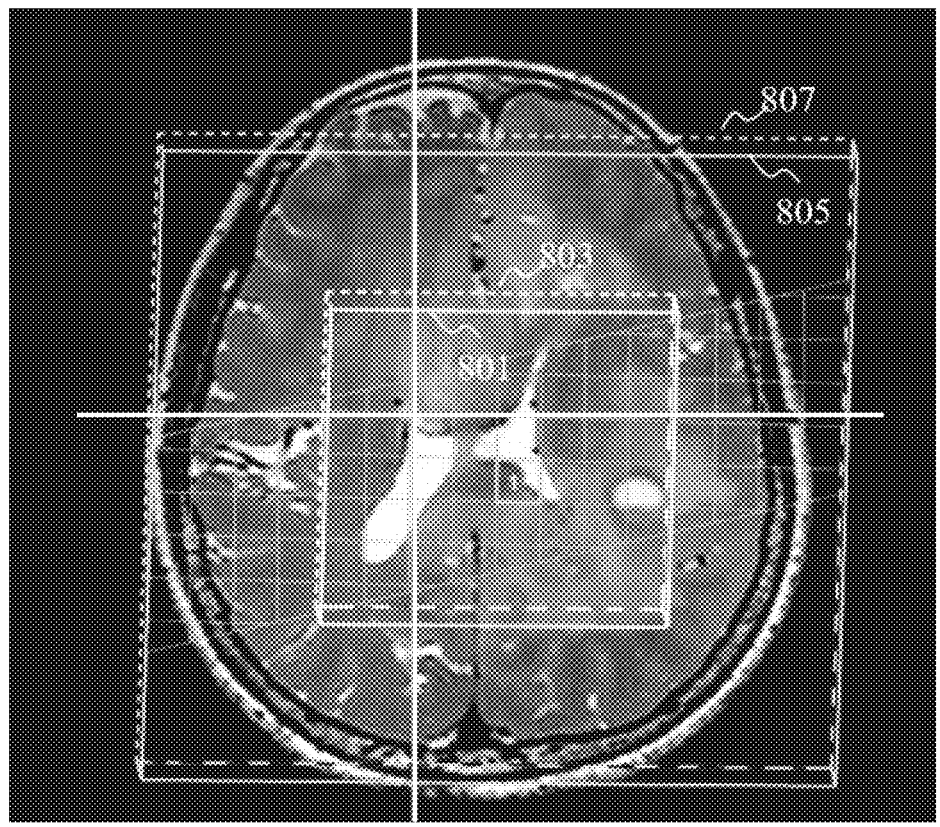
FIG. 8 shows slice information of a scout image and an MRS image affording a transverse view according to some embodiments of the present disclosure.

Example 1 Exemplary MR Image and MRS Image Corresponding to the Brain of a Subject FIG. 8 shows slice information of a scout image and an MRS image affording a transverse view according to some embodiments of the present disclosure. As shown in FIG. 8, solid line frame 801 denotes an MRS image of a region of interest (ROI). Dotted frame 803 denotes a scout image of the ROI. Solid line frame 805 denotes a slice position of the MRS image. Dotted frame 807 denotes a slice position of the scout image. According to FIG. 8, the slice position of the scout image and the slice position of the MRS image are different., i.e., the slice information of the scout image fails to match the slice information of the MRS image.

Figure 9:
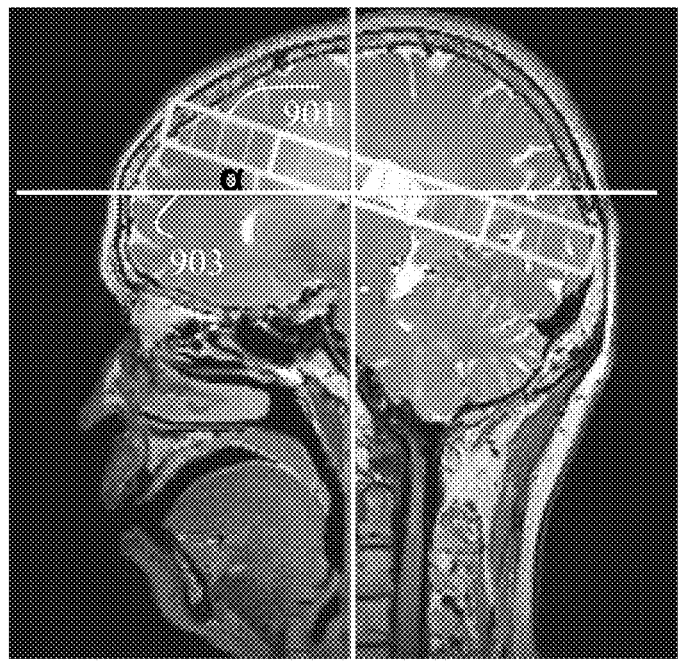
FIG. 9 shows slice information of a scout image and an MRS image affording a sagittal view according to some embodiments of the present disclosure.

Example 2 Exemplary MR Image and MRS Image Corresponding to the Brain of a Subject FIG. 9 shows slice information of a scout image and an MRS image affording a sagittal view according to some embodiments of the present disclosure. As shown in FIG. 9, matrix 901 denotes a slice direction of the MRS image. Line 903 denotes a slice direction of the scout image. According to FIG. 9, an angle $\alpha$ between the slice direction of the MRS image and the slice direction of the scout image was deemed to be non-zero. In other words, the slice information of the MRS image fails to match the slice information of the scout image.

Figure 10:
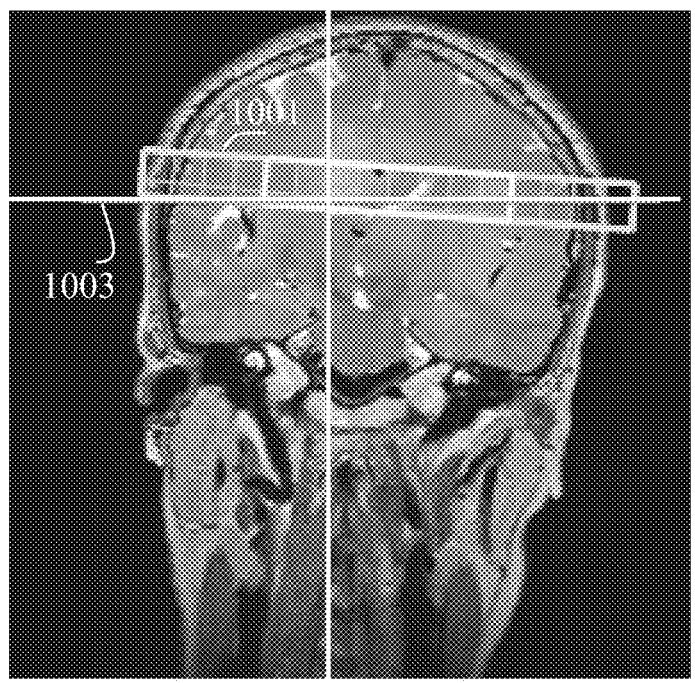
FIG. 10 shows slice information of a scout image and an MRS image affording a coronal view according to some embodiments of the present disclosure.

Example 3 Exemplary MR Image and MRS Image Corresponding to the Brain of a Subject FIG. 10 shows slice information of a scout image and an MRS image affording a coronal view according to some embodiments of the present disclosure. As shown in FIG. 10, matrix 1001 denotes a slice direction of the MRS image. Line 1003 denotes a slice direction of the scout image. According to FIG. 10, an angle between the slice direction of the MRS image and the slice direction of the scout image was deemed to be non-zero. In other words, the slice information of the MRS image fails to match the slice information of the scout image.

Figure 11:
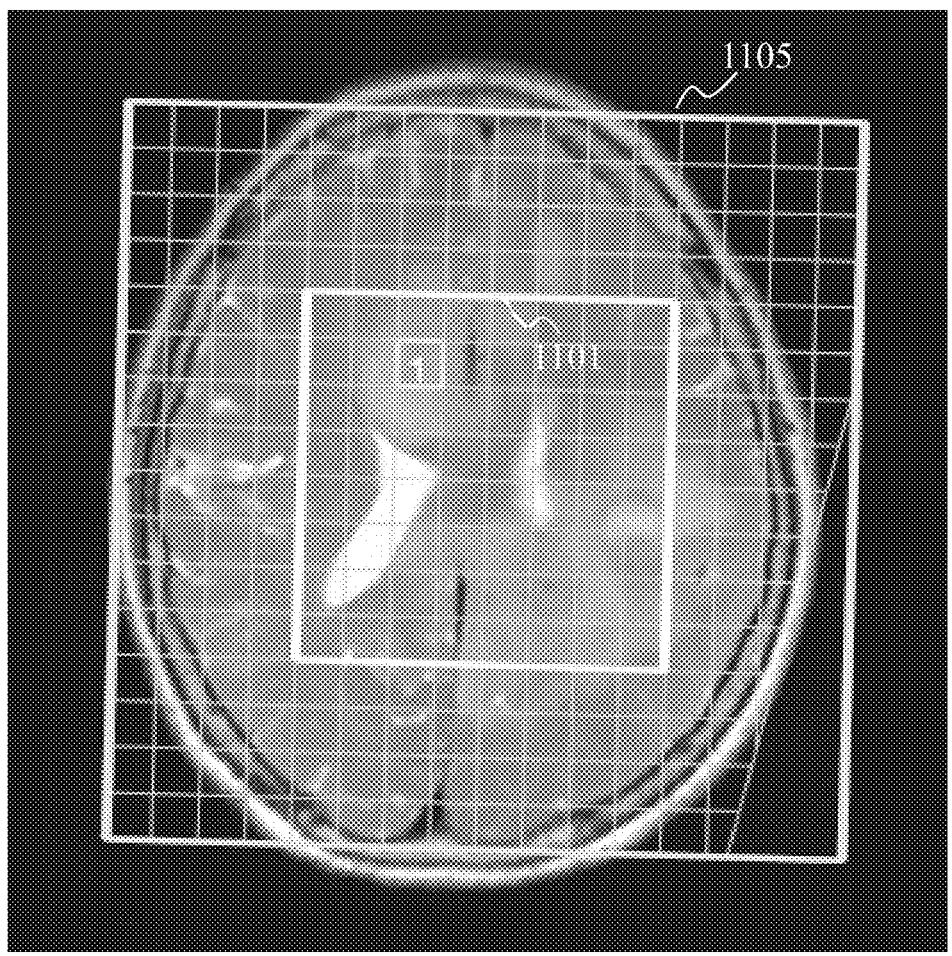
FIG. 11 shows slice information of a reference image and an MRS image affording a transverse view according to some embodiments of the present disclosure.

Example 4 Exemplary MR Image and MRS Image Corresponding to the Brain of a Subject FIG. 11 shows slice information of a reference image and an MRS image affording a transverse view according to some embodiments of the present disclosure. The reference image illustrated in FIG. 11 was obtained by reconstructing the scout image illustrated in FIG. 8. As shown in FIG. 11, solid line frame 1101 denotes the MRS image of the ROI, the same as or similar to the MRS image of the ROI denoted by solid line frame 801 as illustrated in FIG. 8. The reference image of the ROI and the MRS image of the ROI align as illustrated in FIG. 11. Solid line frame 1105 denotes the slice information of the MRS image that matches the slice information of the reference image. The reference numeral "1" in FIG. 11 denotes a pixel in the image.

Figure 12:
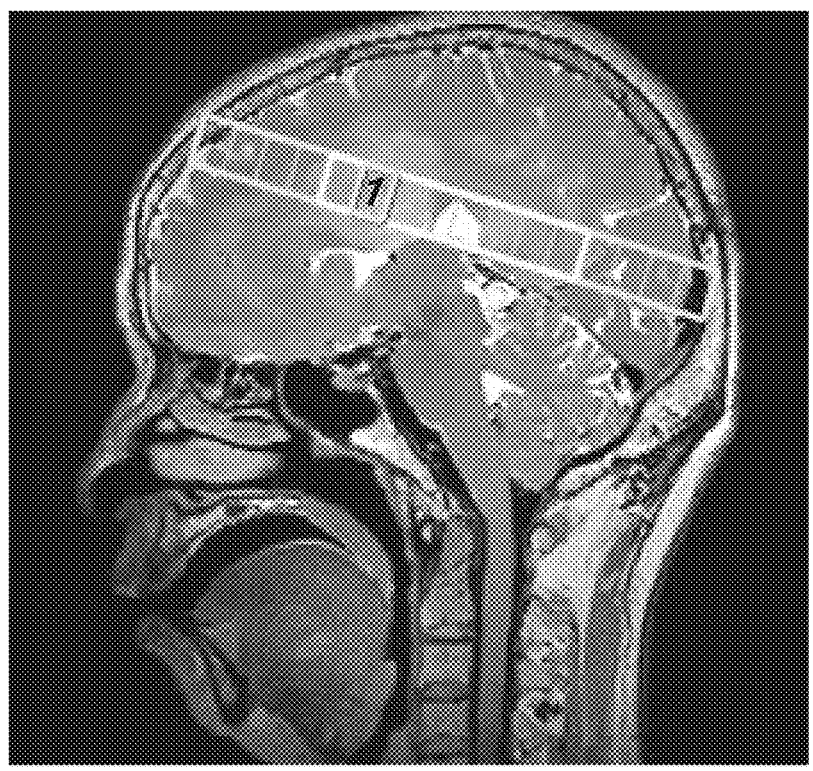
FIG. 12 shows slice information of a reference image and an MRS image affording a sagittal view according to some embodiments of the present disclosure.

Example 5 Exemplary MR Image and MRS Image Corresponding to the Brain of a Subject FIG. 12 shows slice information of a reference image and an MRS image affording a sagittal view according to some embodiments of the present disclosure. The reference image illustrated in FIG. 12 was obtained by reconstructing the scout image illustrated in FIG. 9. As shown in FIG. 12, the slice position of the MRS image matches the slice position of the reference image, and an angle between the slice direction of the MRS image and the slice direction of the reference image was deemed equal to 0°. In other words, the slice information of the MRS image matches the slice information of the reference image. The reference numeral "1" in FIG. 12 denotes a pixel that corresponds to pixel 1 in FIG. 11.

Figure 13:
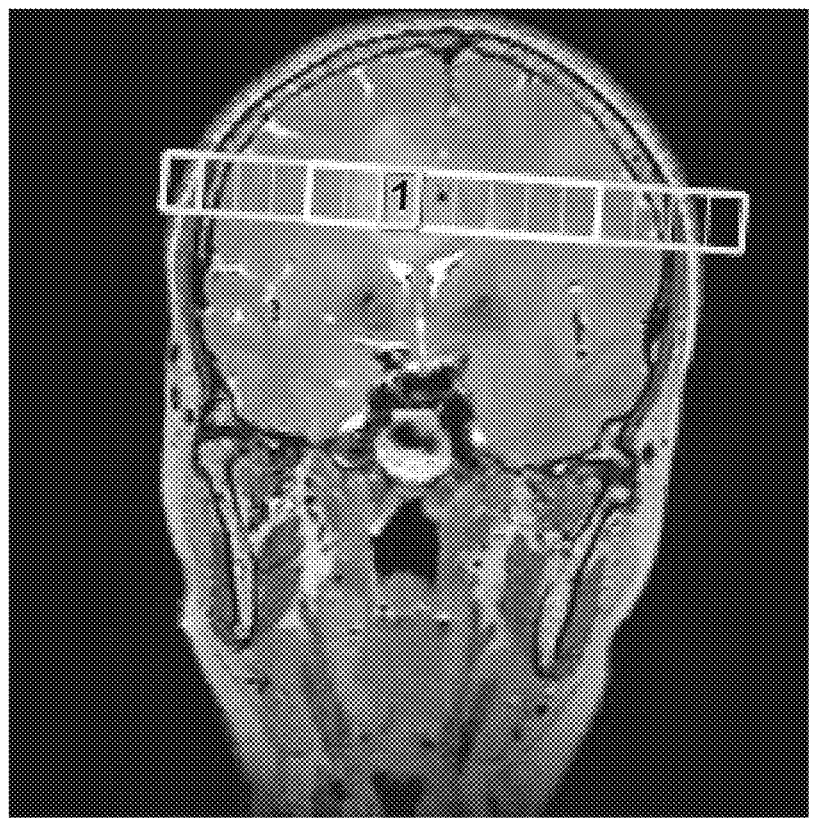
FIG. 13 shows slice information of a reference image and an MRS image affording a coronal view according to some embodiments of the present disclosure.

Example 6 Exemplary MR Image and MRS Image Corresponding to the Brain of a Subject FIG. 13 shows slice information of a reference image and an MRS image affording a coronal view according to some embodiments of the present disclosure. The reference image illustrated in FIG. 13 was obtained by reconstructing the scout image illustrated in FIG. 10. As shown in FIG. 13, the slice position of the MRS image matches the slice position of the reference image, and an angle between the slice direction of the MRS image and the slice direction of the reference image was deemed equal to 0°. In other words, the slice information of the MRS image matches the slice information of the reference image. The reference numeral "1" in FIG. 13 denotes a pixel that corresponds to pixel 1 in FIGS. 11 and 12.

Example 7 Exemplary MRS Image

Figure 14:
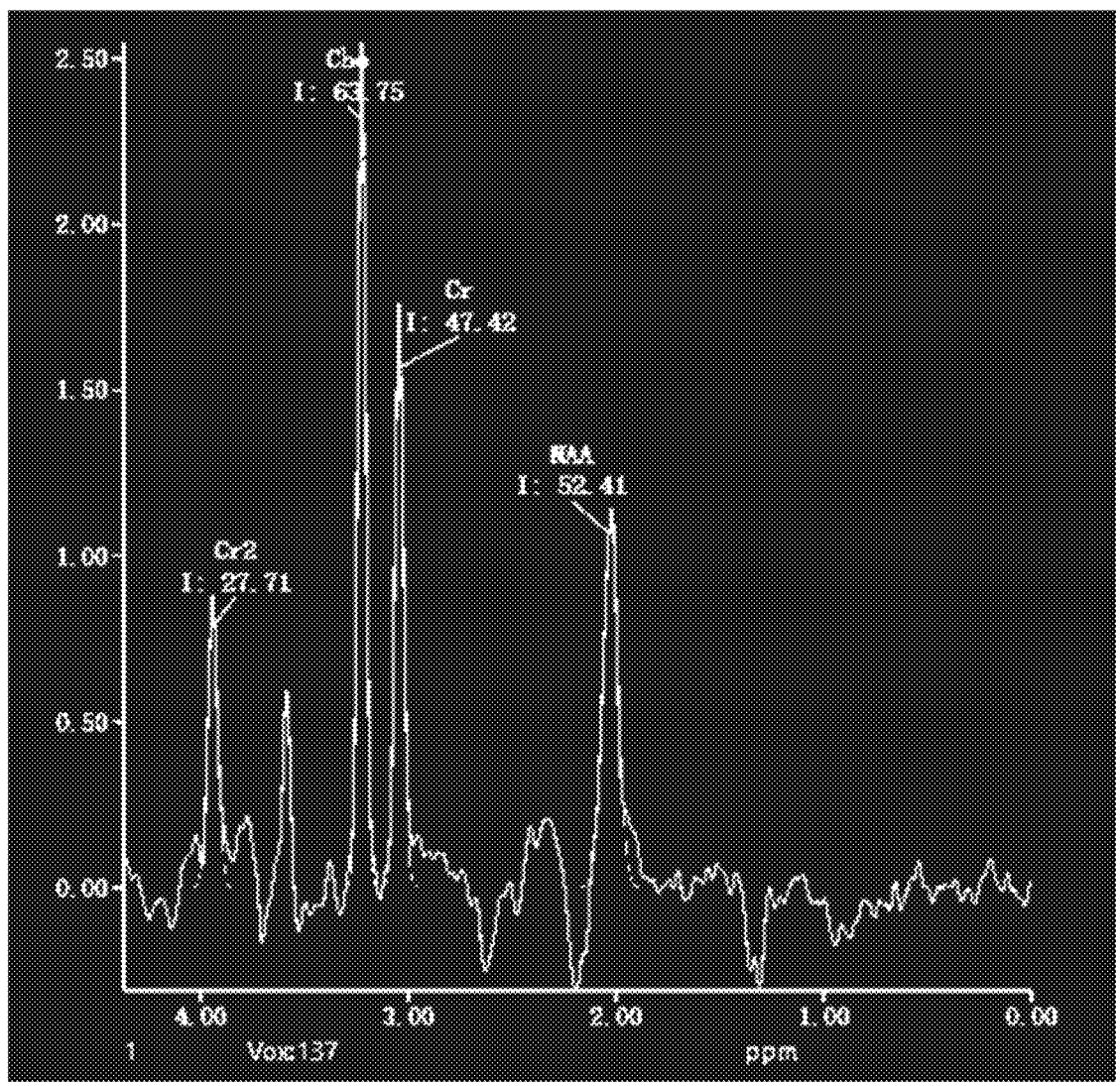
FIG. 14 is a diagram illustrating an exemplary MRS image of a portion of the brain of the same subject as FIGS. 8-13 according to some embodiments of the present disclosure.
Figure 15:
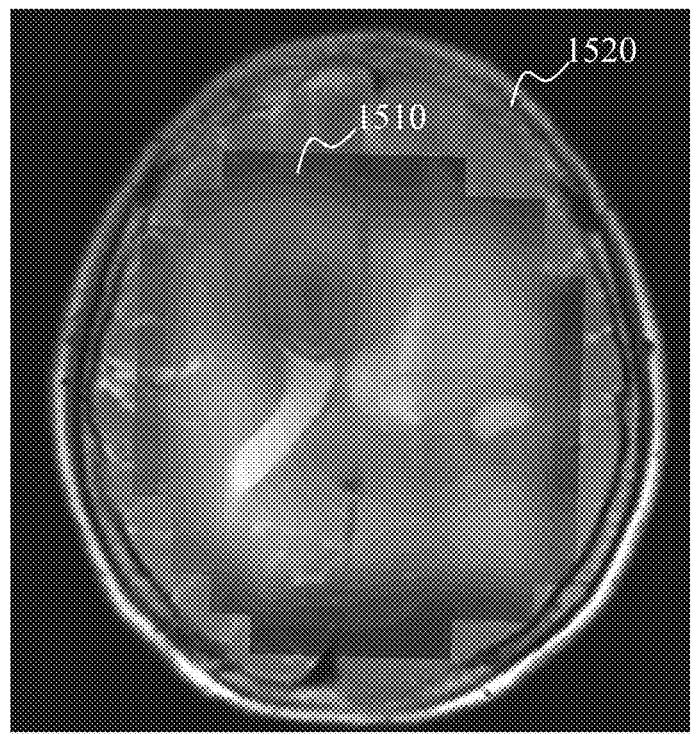
FIGS. 15 to 18 are fused images generated by fusing MRS pseudocolor images and the same reference image according to some embodiments of the present disclosure.
Figure 16:
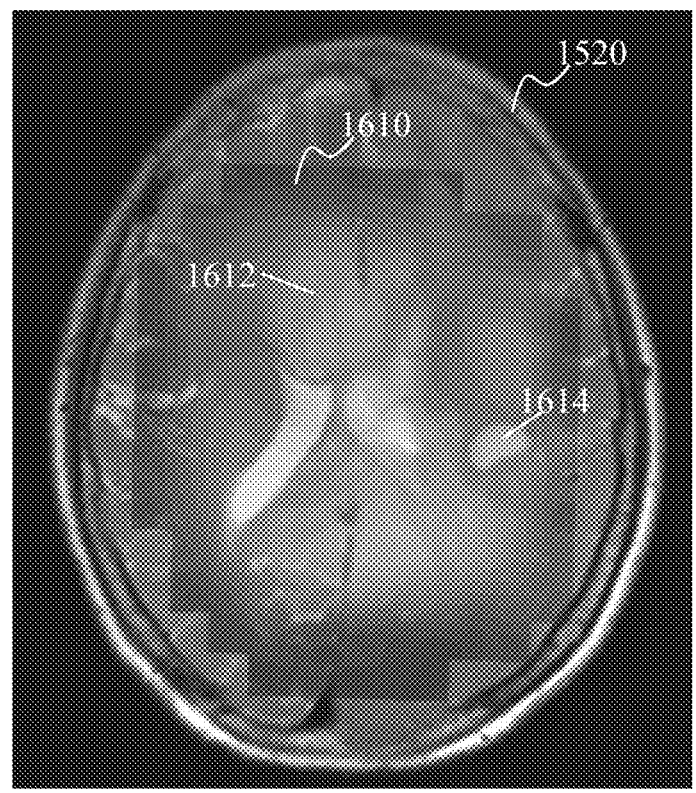
Figure 17:
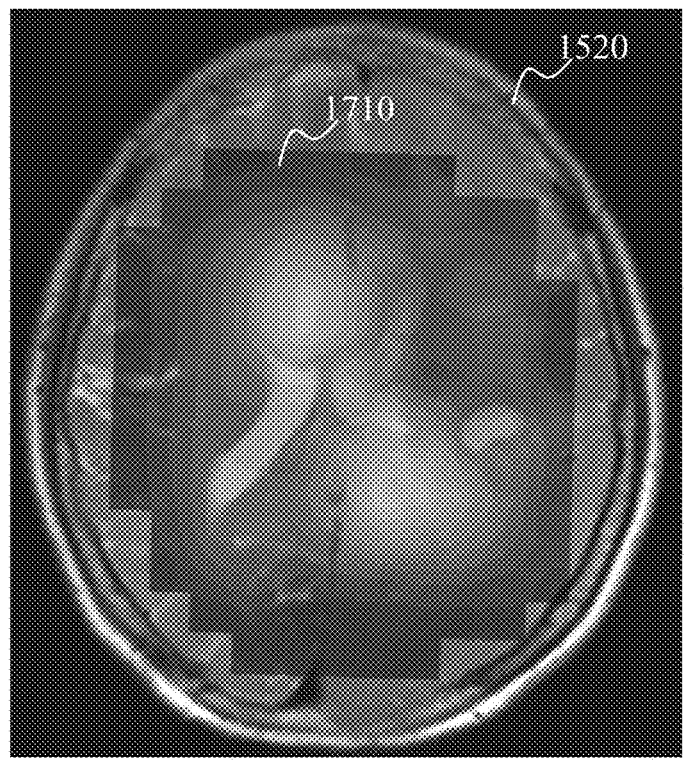
Figure 18:
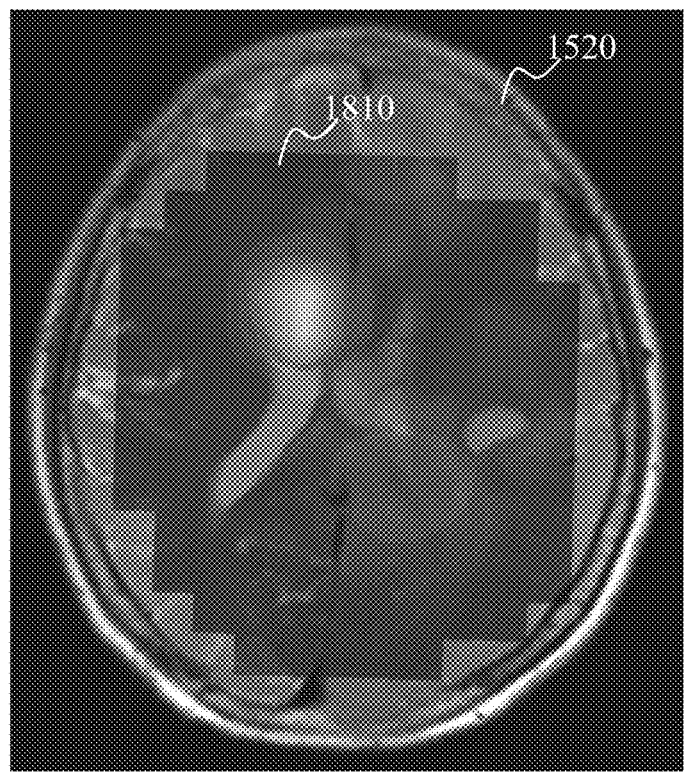

FIG. 14 is a diagram illustrating an exemplary MRS image of a portion of the brain of the same subject as FIGS. 8-13 according to some embodiments of the present disclosure. The MRS image illustrated in FIG. 14 shows a spectrum curve of concentration information of multiple metabolites corresponding to the voxel "1" of the brain illustrated in FIGS. 11-13. Peaks in the spectrum curve demonstrate the multiple metabolites and the concentration information of the multiple metabolites. As shown in FIG. 14, the spectrum curve is presented in a 2-dimensional coordinate system. The X-axis of the 2-dimensional coordinate system represents a category of a metabolite and the Y-axis of the 2-dimensional coordinate system represents concentration information (e.g., integral height) of the metabolite. The portion or position of the subject corresponding to voxel "1" included metabolites, such as N-acetyl aspartate (NAA), creatine (Cr and Cr2), and choline (Cho), etc. NAA is the second-most-concentrated molecule in the brain which mainly exists in neurons. NAA can be used as a biochemical indicator of the severity of neuronal damage. A decrease in the concentration of the NAA may indicate neuronal damage. NAA corresponds to a peak located at 2.03 ppm. The integral (denoted by "I" in FIG. 14) of the peak (also referred to as peak area) corresponding to NAA equals to 52.41. The integral of the peak may be indicative of a count or number of proton (H) of a metabolite, which may reflect the concentration of the metabolite. Creatine is a metabolite of energy whose concentration is relatively stable in the brain. Creatine may be used as an internal reference of the brain for the $^1$H MRS image. For example, a ratio of a certain metabolite to Creatine may reflect a concentration change of the certain metabolite. Creatine may correspond to two peaks in $^1$H MRS image, one of which is located at 3.02 ppm corresponding to Cr, another one is located at 3.94 ppm corresponding to Cr2. The integral (denoted by "I" in FIG. 14) of the peak corresponding to Cr equals to 47.42. The integral (denoted by "I" in FIG. 14) of the peak corresponding to Cr2 equals to 27.71. Cho may mainly exist in the cell membrane whose concentration change may indicate a change in cell membrane metabolism. The concentration of Cho may increase when the cell membrane is degraded or synthesized. Cho corresponds to a peak located at 3.22 ppm. The integral (denoted by "I" in FIG. 14) of the peak corresponding to Cho equals to 63.75. In some embodiments, the concentration of Cho may increase and the concentration of NAA may decrease when there is a tumor in the brain, thereby causing an increase in the ratio of Cho to NAA. A user (e.g., a doctor) may diagnose whether the brain has a lesion based on the concentration of Cho or the ratio of Cho to NAA.

Example 8 Exemplary Fused Images of the Brain of a Subject

FIGS. 15 to 18 are fused images generated by fusing MRS pseudocolor images and the same reference image according to some embodiments of the present disclosure. The reference image 1520 is a T2 weighted image. The MRS pseudocolor images 1510, 1610, 1710, and 1810 include information indicative of a distribution of Cho, NAA, Cr, and a ratio of Cho to NAA, respectively. A location/position of the brain corresponding to each of pixels of the MRS pseudocolor images may be visually recognized/located via the fused images 1510, 1610, 1710, and 1810. Taking the fused image illustrated in FIG. 16 as an example, regions 1612 and 1614 represented in the reference image 1520 include high signals indicating that regions 1612 and 1614 may have lesions. Regions 1612 and 1614 represented in the MRS pseudocolor image 1610 include information indicative of a low concentration of the NAA, consistent with the reference image 1520, which in turn corroborates the diagnosis that regions 1612 and 1614 of the brain of the subject may include tumors.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising:
  at least one storage device storing executable instructions, and
  at least one processor in communication with the at least one storage device, when executing the executable instructions, causing the system to perform operations including:
    obtaining a first image of a first modality representing a first region of the subject, wherein the first image includes a functional image indicative of a distribution of a metabolite in the first region, the first image includes a magnetic resonance spectroscopy (MRS) image;
    generating a pseudocolor image based on the first image, wherein the pseudocolor image includes a plurality of pixels each of which corresponds to a pixel of the first image, each of the pixels in the pseudocolor image has a color that demonstrates the concentration value of a metabolite at a portion or position of the subject, and the color serves as an index or code of the pixel, in which the index or code points to an entry of a color look-up table (CLUT);
    obtaining a second image by processing pixel values of pixels in an additional image using an interpolation function, the interpolation function including one or more coefficients associated with a deviation between slice information of the first image and slice information of the additional image, the additional image including a structural image indicative of one or more structural characteristics of a second region, the second image representing the second region of the subject, the second region including at least part of the first region of the subject, a slice direction of the additional image failing to match a slice direction of the first image, the slice direction of the first image being same as a slice direction of the second image; and generating a fused image by fusing the pseudocolor image and the second image, wherein the fused image includes a fusion of the second image and the distribution of the metabolite indicated by the first image.

2. The system of claim 1, wherein to obtain a first image of a first modality representing a first region of a subject, the at least one processor is further configured to cause the system to perform the operations including:

obtaining one or more scout images of the first region of the subject; and causing an imaging device to acquire the first image by scanning the first region of the subject according to the one or more scout images.

3. The system of claim 2, wherein the at least one processor is further configured to cause the system to perform the operations including:

determining whether one of the one or more scout images and the first image misalign; and in response to a determination that the one of the one or more scout images and the first image misalign, obtain the additional image including the first region of the subject;

obtaining the second image by processing the pixel values of pixels in the additional image using the interpolation function; and generating the fused image by fusing the pseudocolor image and the second image.

4. The system of claim 3, wherein to determine whether one of the one or more scout images and the first image misalign, the at least one processor is further configured to cause the system to perform the operations including:

determining whether slice information of the one of the one or more scout images matches slice information of the first image, the slice information including at least one of a slice position or a slice direction; and determining that the one of the one or more scout images and the first image misalign in response to a determination that the slice information of the one of the one or more scout images fails to match the slice information of the first image.

5. The system of claim 2, wherein the additional image includes at least one of the one or more scout images.

6. The system of claim 1, wherein the additional image and the first image are of different modalities.

7. The system of claim 1, wherein to generate the fused image by fusing the pseudocolor image and the second image, the at least one processor is further configured to cause the system to perform the operations including:

generating a registered pseudocolor image by registering the pseudocolor image with the second image; and fusing the registered pseudocolor image and the second image to obtain the fused image.

8. The system of claim 2, wherein the at least one processor is further configured to cause the system to perform the operations including:

determining whether one of the one or more scout images and the first image misalign; and in response to a determination that the one of the one or more scout images and the first image align, fusing the first image and the one of the one or more scout images.

9. A method implemented on a computing device having at least one processor and at least one storage device, the method comprising:

obtaining a first image of a first modality representing a first region of the subject, wherein the first image includes a functional image indicative of a distribution of a metabolite in the first region, the first image includes a magnetic resonance spectroscopy (MRS) image;

generating a pseudocolor image based on the first image, wherein the pseudocolor image includes a plurality of pixels each of which corresponds to a pixel of the first image, each of the pixels in the pseudocolor image has a color that demonstrates the concentration value of a metabolite at a portion or position of the subject, and the color serves as an index or code of the pixel, in which the index or code points to an entry of a color look-up table (CLUT);

obtaining a second image of by processing pixel values of pixels in the additional image using an interpolation function, the interpolation function including one or more coefficients associated with a deviation between slice information of the first image and slice information of the additional image, the additional image including a structural image indicative of one or more structural characteristics of a second region, the second image representing the second region of the subject, the second region including at least part of the first region of the subject, a slice direction of the additional image failing to match a slice direction of the first image, the slice direction of the first image being same as a slice direction of the second image; and generating a fused image by fusing the pseudocolor image and the second image, wherein the fused image includes a fusion of the second image and the distribution of the metabolite indicated by the first image.

10. The method of claim 9, wherein obtaining a first image of a first modality representing a first region of a subject includes:

obtaining one or more scout images of the first region of the subject; and causing an imaging device to acquire the first image by scanning the first region of the subject according to the one or more scout images.

11. The method of claim 10, wherein the additional image includes at least one of the one or more scout images.

12. The method of claim 9, wherein the additional image and the first image are of different modalities.

13. A non-transitory computer readable medium, comprising a set of instructions, wherein when executed by at least one processor, the set of instructions direct the at least one processor to effectuate a method, the method comprising:

obtaining a first image of a first modality representing a first region of the subject, wherein the first image includes a functional image indicative of a distribution of a metabolite in the first region, the first image includes a magnetic resonance spectroscopy (MRS) image;

generating a pseudocolor image based on the first image, wherein the pseudocolor image includes a plurality of pixels each of which corresponds to a pixel of the first image, each of the pixels in the pseudocolor image has a color that demonstrates the concentration value of a metabolite at a portion or position of the subject, and the color serves as an index or code of the pixel, in which the index or code points to an entry of a color look-up table (CLUT);

obtaining a second image by processing pixel values of pixels in the additional image using an interpolation function, the interpolation function including one or more coefficients associated with a deviation between slice information of the first image and slice information of the additional image, the additional image including a structural image indicative of one or more structural characteristics of a second region, the second image representing the second region of the subject, the second region including at least part of the first region of the subject, a slice direction of the additional image failing to match a slice direction of the first image, the slice direction of the first image being same as a slice direction of the second image; and generating a fused image by fusing the pseudocolor image and the second image, wherein the fused image includes a fusion of the second image and the distribution of the metabolite indicated by the first image.

\* \* \* \* \*